United States Patent
Ali et al.

(10) Patent No.: US 9,940,440 B2
(45) Date of Patent: Apr. 10, 2018

(54) DETECTING AND RESPONDING TO SOFTWARE AND HARDWARE ANOMALIES IN A FLUID DELIVERY SYSTEM

(75) Inventors: Irfan Z. Ali, Woodbury, MN (US); Donald L. Villalta, Minneapolis, MN (US); Scott A. Sarkinen, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 2112 days.

(21) Appl. No.: 13/096,756

(22) Filed: Apr. 28, 2011

(65) Prior Publication Data

US 2012/0277716 A1 Nov. 1, 2012

(51) Int. Cl.
*A61M 5/168* (2006.01)
*G06F 19/00* (2018.01)
*A61M 5/142* (2006.01)

(52) U.S. Cl.
CPC ..... *G06F 19/3468* (2013.01); *A61M 5/14276* (2013.01); *A61M 2005/14208* (2013.01); *A61M 2205/18* (2013.01); *A61M 2205/3523* (2013.01); *A61M 2205/3561* (2013.01); *A61M 2205/3569* (2013.01); *A61M 2205/50* (2013.01)

(58) Field of Classification Search
CPC ............. A61M 5/168; A61M 5/16831; A61M 2205/18; A61M 2005/14208; G06F 19/3468
USPC ............................................. 604/65, 67, 151
See application file for complete search history.

(56) References Cited

U.S. PATENT DOCUMENTS

| | | | |
|---|---|---|---|
| 3,701,345 | A | 10/1972 | Heilman et al. |
| 4,047,844 | A | 9/1977 | Robinson |
| 4,308,866 | A | 1/1982 | Jelliffe et al. |
| 4,715,852 | A | 12/1987 | Reinicke et al. |

(Continued)

FOREIGN PATENT DOCUMENTS

WO WO 2009048462 A1 * 4/2009
WO 2009103492 A1 8/2009

OTHER PUBLICATIONS

U.S. Appl. No. 61/165,467, filed Mar. 31, 2009, 33 pages, Wilinska et al., entire document.

(Continued)

*Primary Examiner* — Emily Schmidt
*Assistant Examiner* — Amber Stiles
(74) *Attorney, Agent, or Firm* — Shumaker & Sieffert, P.A.

(57) ABSTRACT

A total dose of a therapeutic agent to be delivered to a patient by an infusion device over a total period of time is automatically divided into a plurality of unit doses to be delivered to the patient over a plurality of unit periods of time. The infusion device is automatically programmed to deliver one of the unit doses of the therapeutic agent to the patient over its respective unit period of time, after which the one unit dose is delivered, and a determination is made of whether an error occurred in delivering the one unit dose to the patient. Delivery of the total dose of the therapeutic agent to the patient may include iteratively automatically programming the infusion device to deliver successive unit doses upon determining that no error occurred in delivering a previous unit dose to the patient. Accordingly, the risk of improperly dosing the patient with the therapeutic agent in an event of a software or hardware anomaly within the infusion device is prevented or reduced.

54 Claims, 4 Drawing Sheets

(56) References Cited

U.S. PATENT DOCUMENTS

| | | |
|---|---|---|
| 4,731,051 A | 3/1988 | Fischell |
| 5,181,910 A | 1/1993 | Scanlon |
| 5,472,614 A | 12/1995 | Rossi |
| 5,582,593 A | 12/1996 | Hultman |
| 5,712,795 A | 1/1998 | Layman et al. |
| 5,800,387 A | 9/1998 | Duffy et al. |
| 5,947,907 A | 9/1999 | Duich |
| 5,973,968 A | 10/1999 | Schu et al. |
| 6,083,187 A | 7/2000 | Nakayama et al. |
| 6,562,001 B2 | 5/2003 | Lebel et al. |
| 6,571,128 B2 | 5/2003 | Lebel et al. |
| 6,635,048 B1 | 10/2003 | Ullestad et al. |
| 6,796,956 B2 | 9/2004 | Hartlaub et al. |
| 7,128,729 B2 | 10/2006 | Duchon et al. |
| 7,338,464 B2 | 3/2008 | Blischak et al. |
| 7,505,869 B2 | 3/2009 | Hartlaub |
| 7,913,496 B2 | 3/2011 | Batenburg et al. |
| 8,057,492 B2 | 11/2011 | Ortiz et al. |
| 8,062,249 B2 | 11/2011 | Wilinska et al. |
| 8,262,617 B2 | 9/2012 | Aeschlimann et al. |
| 8,323,245 B2 | 12/2012 | List et al. |
| 2002/0156464 A1 | 10/2002 | Blischak et al. |
| 2003/0217747 A1 | 11/2003 | Hickle et al. |
| 2004/0220517 A1 | 11/2004 | Starkweather et al. |
| 2005/0049656 A1 | 3/2005 | Petersen et al. |
| 2005/0187515 A1 | 8/2005 | Varrichio et al. |
| 2006/0173444 A1 | 8/2006 | Choy et al. |
| 2006/0184154 A1* | 8/2006 | Moberg et al. .............. 604/506 |
| 2006/0258985 A1* | 11/2006 | Russell ............. A61M 5/14212 |
| | | 604/151 |
| 2008/0126969 A1 | 5/2008 | Blomquist |
| 2009/0043290 A1 | 2/2009 | Villegas et al. |
| 2009/0112155 A1* | 4/2009 | Zhao et al. .................... 604/67 |
| 2009/0137956 A1 | 5/2009 | Souter |
| 2010/0081993 A1* | 4/2010 | O'Connor .................... 604/151 |
| 2010/0094221 A1* | 4/2010 | Spencer et al. .............. 604/151 |
| 2010/0094261 A1 | 4/2010 | Bryant et al. |
| 2011/0172633 A1 | 7/2011 | Ali et al. |
| 2012/0157920 A1 | 6/2012 | Flachbart et al. |

OTHER PUBLICATIONS

Zhang et al., "A hazard analysis for a generic insulin infusion pump," Journal of Diabetes Science and Technology, vol. 4, No. 2, pp. 263-283, Mar. 2010.

International Search Report and Written Opinion of international application No. PCT/US2012/032001, dated Nov. 13, 2012, 19 pp.

\* cited by examiner

DETECTING AND RESPONDING TO SOFTWARE AND HARDWARE ANOMALIES IN A FLUID DELIVERY SYSTEM

TECHNICAL FIELD

The disclosure relates generally to implantable fluid delivery devices.

BACKGROUND

Implantable fluid delivery devices are used to treat a number of physiological, psychological, and emotional conditions, including chronic pain, tremor, Parkinson's disease, epilepsy, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a fluid therapeutic agent (e.g., a drug in fluid form). The implantable fluid delivery device typically includes a reservoir, a fill port used to fill the reservoir with a therapeutic agent, a pumping mechanism used to pump the therapeutic agent from the reservoir, a catheter port used to transport the therapeutic agent from the reservoir via a catheter to a desired location within the patient's body, and electronics used to control the pumping mechanism. The implantable fluid delivery device also typically includes some form of fluid flow control in order to control or regulate the flow of the therapeutic agent from the reservoir to the catheter port for delivery of the therapeutic agent to the desired location within the patient's body. Implantable fluid delivery devices are generally used as part of a fluid delivery system, which may include additional components, such as an external programmer used to interact with the implantable fluid delivery device.

SUMMARY

In general, this disclosure relates to systems and methods for preventing or reducing the risk of improperly dosing a patient with a therapeutic agent in a case of software or hardware anomaly of a fluid delivery system including an implantable fluid delivery device (hereinafter "infusion device") used to deliver the agent to the patient.

In one example, a method includes receiving a total dose of a therapeutic agent to be delivered to a patient by an infusion device over a total period of time, automatically dividing the total dose into a plurality of unit doses, each of which is equal to a fraction of the total dose configured to be delivered to the patient by the infusion device over a unit period of time equal to a fraction of the total period of time, automatically programming the infusion device to deliver to the patient one of the plurality of unit doses over its respective unit period of time, delivering to the patient, by the infusion device, the one unit dose, and determining whether an error has occurred in delivering the one unit dose to the patient.

In another example, a fluid delivery system includes a pump, a memory, and a processor. The pump is configured to deliver a therapeutic agent to a patient. The memory contains a total dose of the therapeutic agent to be delivered to the patient by the pump over a total period of time. The processor is configured to automatically divide the total dose into a plurality of unit doses, each of which is equal to a fraction of the total dose configured to be delivered to the patient by the pump over a unit period of time equal to a fraction of the total period of time, automatically control the pump to deliver to the patient one of the plurality of unit doses over its respective unit period of time, and determine whether an error has occurred in delivering the one unit dose to the patient.

In another example, a computer-readable storage medium includes instructions for causing a programmable processor to receive a total dose of a therapeutic agent to be delivered to a patient by an infusion device over a total period of time, automatically divide the total dose into a plurality of unit doses, each of which is equal to a fraction of the total dose configured to be delivered to the patient by the infusion device over a unit period of time equal to a fraction of the total period of time, automatically program the infusion device to deliver to the patient one of the plurality of unit doses over its respective unit period of time, deliver to the patient, by the infusion device, the one unit dose, and determine whether an error has occurred in delivering the one unit dose to the patient.

In another example, a system includes means for receiving a total dose of a therapeutic agent to be delivered to a patient by an infusion device over a total period of time, means for automatically dividing the total dose into a plurality of unit doses, each of which is equal to a fraction of the total dose configured to be delivered to the patient by the infusion device over a unit period of time equal to a fraction of the total period of time, means for automatically programming the infusion device to deliver to the patient one of the plurality of unit doses over its respective unit period of time, means for delivering to the patient, by the infusion device, the one unit dose, and means for determining whether an error has occurred in delivering the one unit dose to the patient.

The details of one or more examples are set forth in the accompanying drawings and the description below. Other features, objects, and advantages of examples according to this disclosure will be apparent from the description and drawings, and from the claims.

DETAILED DESCRIPTION

Figure 1:
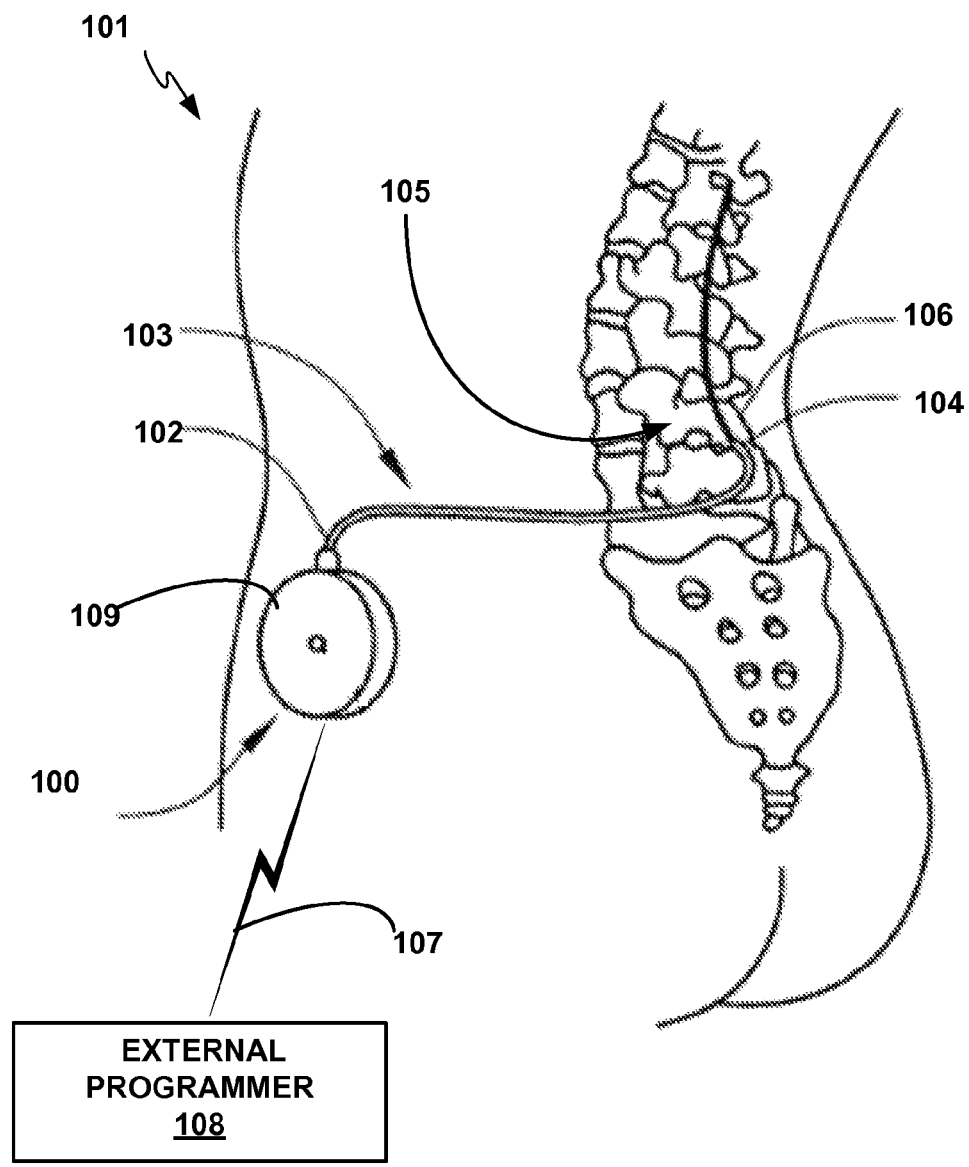
FIG. 1 is a conceptual diagram illustrating an example of a fluid delivery system, which includes an external programmer and an infusion device, configured to deliver a therapeutic agent to a patient via a catheter.

Infusion devices are commonly configured to deliver a therapeutic agent to a patient according to one or more therapy programs that define particular therapy parameters for the delivery of the agent to the patient. Such therapy parameters may include an infusion schedule, which may, for example, specify one or more doses (e.g., measured in microliters, micrograms (mcg), or other volumetric or mass units) of the therapeutic agent to be delivered to the patient by the device over one or more periods of time (e.g., per day or over an hour-long period). Such therapy parameters may also define handling of patient-initiated boluses, specify infusion limits, and so forth. Typically, the therapy parameters are entered into the infusion device with the aid of an external programming device, which may be a clinician or a patient programmer.

The electronics of an infusion device may include a processor and other associated hardware configured to deliver the therapeutic agent to the patient according to the therapy parameters. The device may also include some form of memory, such as a Read-Only Memory (ROM), Random Access Memory (RAM), and/or a non-volatile memory, such as electrically-erasable programmable ROM (EE-PROM) or FLASH memory, for storing, among other information, the therapy parameters. After the infusion device is implanted in a patient, a number of complications may occur that affect the ability of the device to reliably deliver the therapeutic agent to the patient according to the therapy parameters. For example, the device memory that stores the parameters and processor registers used to execute software instructions associated with the parameters may become corrupted.

Memory and register corruption can occur for several reasons. For example, memory and register corruption can be caused by a temporary drop in the voltage of the infusion device power source (e.g., battery or power conversion circuit voltage drops due to Electro-Magnetic Interference (EMI) or an internal power surge), software execution malfunctions (e.g., a bug or bit flip within the memory or processor registers, such as bit flip errors due to EMI or exposure to radiation or cosmic rays, that causes an erroneous program execution), or latent memory cell or register location failures in which one or more memory cells or register locations lose their ability to retain programmed data over time (e.g., memory cells may be unable to retain data written to the cells, and processor register locations may be unable to be written to or modified by processor operations according to one or more software instructions). Whatever the cause, memory and register corruption may result in incorrect therapy parameters to be stored in the memory and/or processed by the processor of the infusion device when delivering the therapeutic agent to the patient.

Additionally, even when the processor and memory (collectively "hardware") components of the device are functioning properly, software computational errors within the clinician programmer or the infusion device may result in specifying incorrect therapy parameters for the delivery of the therapeutic agent to the patient. In both cases of hardware and software malfunction affecting proper delivery of therapy to the patient, the patient may receive an undesirable overdose or underdose of the therapeutic agent, which may result in adverse effects on the patient's health.

Because of the potential modes of software and hardware malfunction of a fluid delivery system set forth above, some techniques for delivering a therapeutic agent to a patient using an infusion device may suffer from certain drawbacks. For example, delivering the agent to the patient using the infusion device according to an infusion schedule or a patient-initiated bolus request that specifies one or more doses of the agent to be delivered to the patient over one or more time periods creates a risk of delivering an overdose or an underdose of the agent to the patient in the event of device malfunction.

In one example, a software or hardware malfunction within the infusion device may render the device unable to stop delivering the one or more programmed doses at the end of their respective time periods, abort the delivery of the one or more doses according to a user input, or cause the device to deliver the one or more doses in shorter time periods (i.e., at a greater infusion rate, resulting in an overdose), or longer time periods (i.e., at a lower infusion rate, resulting in an underdose) than specified.

In other examples, an error (e.g., software or hardware error) occurring in an external programmer of the associated fluid delivery system, in the transmission of data between the external programmer and the infusion device, or in any other stage within the system whereby the effective requested dose is other than that which would be appropriate for the patient, may cause an overdose or underdose of the therapeutic agent to be delivered to the patient.

As stated above, this disclosure is directed to techniques for preventing or reducing the risk of improperly dosing a patient with a therapeutic agent in a case of software or hardware malfunction of a fluid delivery system including an infusion device used to deliver the agent to the patient. The following examples include receiving a total dose of the therapeutic agent to be delivered to the patient by the infusion device over a total period of time. The total dose may be any programmed dose that is requested to be delivered by the infusion device to the patient, including, e.g. a constant dose delivered over the course of hours, days, or weeks that is part of an infusion schedule, one dose to be delivered over the course of hours, days, or weeks that is one of multiple programmed doses in a time varying infusion schedule, or a dose defined by a patient or other supplemental bolus. The total dose is automatically divided into a plurality of therapeutically-safe unit doses to be delivered to the patient over a plurality of unit periods of time. The infusion device is automatically programmed to deliver one of the unit doses of the therapeutic agent to the patient over its respective unit period of time, after which delivery of the therapeutic agent to the patient by the infusion device is stopped. Delivery of the total dose of the therapeutic agent to the patient requires iteratively automatically programming the infusion device to deliver successive unit doses over their respective unit periods of time until the total dose is delivered, or until the total period of time elapses.

In the foregoing manner, automatically dividing the total dose into the plurality of unit doses and automatically programming the infusion device to deliver to the patient one of the plurality of unit doses at one time according to this disclosure may effectively prevent or limit the consequences of a software or hardware malfunction of a fluid delivery system including the infusion device by reducing the time over which the agent can be delivered to the patient according to a particular set of therapy parameters. For example, rather than delivering the agent to the patient according to the total dose to be delivered over the total period of time, as defined by an infusion schedule or a patient-initiated bolus request, the infusion device is operable to deliver the agent according to only a portion (e.g., a fraction of the total dose) of the infusion schedule or patient-initiated bolus request and requires further instruction before continuing to deliver the agent. For example, delivery of an additional amount of the agent to the patient requires further operation by the device to deliver successive unit doses into which the total dose has been divided, upon completion of which no additional amount of the agent will be delivered, and so forth.

Accordingly, a fluid delivery system including an infusion device configured in accordance with this disclosure may therefore prevent or reduce the risk of delivering an amount of a therapeutic agent to a patient in excess of the amount corresponding to one of the unit doses into which the total dose has been divided in the event of a software or hardware malfunction. Additionally, the risk of an overdose or underdose of the agent to the patient may be further reduced by limiting the delivery of the agent to the patient according to one or more threshold values, including, e.g., a maximum unit dose. The disclosed techniques also include stopping the delivery altogether and/or alerting the patient in the event the delivery of the agent to the patient exceeds any of the one or more thresholds.

FIG. 1 is a conceptual diagram illustrating an example fluid delivery system consistent with one or more aspects of this disclosure, including an infusion device 100 (hereinafter "device 100"), which is configured to deliver a therapeutic agent, such as a pharmaceutical agent, e.g., a drug, insulin, pain relieving agent, anti-inflammatory agent, gene therapy agent, or the like to a target site 105 within a patient 101. The therapeutic agent is delivered via a catheter 103 that is fluidly coupled to device 100. Catheter 103 may comprise a plurality of catheter segments, or catheter 103 may be a unitary catheter. In the example illustrated in FIG. 1, target site 105 is proximate to a spinal cord 106 of patient 101. In other examples, target site 105 may be located elsewhere within patient 101. As shown in FIG. 1, a proximal end 102 of catheter 103 is coupled to device 100 while a distal end 104 of catheter 103 is positioned proximate to target site 105.

As further shown in FIG. 1, the fluid delivery system may also include an external programmer 108 (hereinafter "programmer 108") that communicates with device 100 as needed, such as to provide to device 100 therapy parameters defining the delivery of the agent to patient 101, or retrieve information associated with the delivery of therapy or relating to status of device 100. For example, programmer 108 may be configured to turn device 100 on or off, to deliver initial therapy parameters for patient 101, to modify the therapy parameters, receive information regarding status of device 100, and so forth. In one example, shown in FIG. 1, programmer 108 communicates with device 100 using a wireless communication link 107.

Although patient 101 is generally referred to as a human patient in the present disclosure, the fluid delivery system can be used with other mammalian or non-mammalian patients. Additionally, device 100 may be employed to treat, manage or otherwise control various conditions or disorders of patient 101, including, e.g., pain (e.g., chronic pain, post-operative pain, or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders.

Additionally, device 100 may be configured to deliver one or more therapeutic agents, alone or in combination with other therapies, including, e.g., electrical stimulation. For example, in some cases, device 100 may deliver one or more pain-relieving drugs to patients with chronic pain, insulin to patients with diabetes, or other fluids to patients with other disorders. For example, device 100 may be implanted in patient 101 for delivering long-term or temporary therapy.

As further shown in FIG. 1, device 100 includes an outer housing 109 that is constructed of a biocompatible material that resists corrosion and degradation from bodily fluids, e.g. titanium or biologically-inert polymers. Device 100 may be implanted within a subcutaneous pocket close to target site 105. For example, as shown in FIG. 1, device 100 may be implanted within the abdomen of patient 101 close to a location along spinal cord 106 where target site 105 is located. In other examples, device 100 may be implanted within other suitable locations within patient 101, which may depend, for example, on where target site 105 is located within patient 101 and the ease of implanting device 100 within the locations. Device 100 may also be external to patient 101, with a percutaneous catheter 103 connected between device 100 and target site 105 within patient 101.

Additionally, catheter 103 may be coupled to device 100 either directly or with the aid of a catheter extension (not shown). In the example shown in FIG. 1, catheter 103 traverses from the implant site of device 100 to target site 105 proximate to spinal cord 106. Catheter 103 is positioned such that one or more fluid delivery outlets of catheter 103 are proximate to the one or more locations at target site 105 within patient 101. Device 100 delivers a therapeutic agent to target site 105 proximate to spinal cord 106 with the aid of catheter 103. For example, device 100 may be configured for intrathecal drug delivery into the intrathecal space or epidural space surrounding spinal cord 106.

In some examples, multiple catheters may be coupled to device 100 to target the same or different tissue or nerve sites within patient 101. Thus, although a single catheter 103 is shown in FIG. 1, in other examples, the fluid delivery system consistent with one or more aspects of this disclosure may include multiple catheters, or catheter 103 may include multiple lumens for delivering different therapeutic agents to patient 101 or for delivering a therapeutic agent to different target sites within patient 101. Accordingly, in some examples, device 100 may include a plurality of reservoirs for storing more than one type of therapeutic agent. However, for ease of description, device 100 including a single reservoir containing a single type of therapeutic agent, and a single catheter 103, are primarily discussed herein with reference to the example of FIG. 1. In some additional examples, device 100 may include a single long tube that contains the therapeutic agent in place of a reservoir.

Device 100 may deliver one or more therapeutic agents to patient 101 according to one or more therapy programs. Example therapeutic agents that device 100 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications, and chemotherapeutics. A therapy program, generally speaking, may set forth different therapy parameters, such as an infusion schedule specifying one or more doses of a therapeutic agent to be delivered to a patient by an infusion device over one or more periods of time, as well as define handling of patient-initiated boluses, specify infusion limits, and so forth.

The therapy programs may be a part of a program group for therapy of patient 101, wherein the group includes a plurality of constituent therapy programs. In some examples, device 100 may be configured to deliver a therapeutic agent to patient 101 according to different therapy programs on a selective basis. Device 100 may include a memory to store one or more therapy programs, and instructions defining the extent to which patient 101 may adjust therapy parameters of the therapy programs, switch between therapy programs, or undertake other therapy adjustments. Patient 101 may select and/or generate additional therapy programs for use by device 101 via programmer 108 at any time during therapy or as designated by a clinician.

As discussed above, the fluid delivery system shown in FIG. 1 also includes programmer 108. Programmer 108 is a computing device configured to wirelessly communicate with device 101. For example, programmer 108 may be a programmer of a clinician used by the clinician to communicate with device 100 to provide therapy parameters to device 100 and receive status information from device 100. Alternatively, programmer 108 may be a programmer of patient 101 used by patient 101 to view, define, and modify various therapy parameters of device 100 and receive status information from device 100. The clinician programmer may include additional or alternative programming features, relative to the features of the patient programmer. For example, more complex or sensitive tasks may only be allowed to be performed by the clinician programmer to reduce the risk that patient 101 makes undesired changes to the operation of device 100.

Programmer 108 may be a hand-held computing device that includes a display viewable by a user (e.g., a clinician or a patient) that can be used to provide to the user status information relating to operation of programmer 108, and a user input mechanism that can be used to provide input from the user to programmer 108. For example, programmer 108 may include a display (e.g., a liquid crystal display (LCD) or a light emitting diode (LED) display) that presents information to the user. In addition, programmer 108 may include a keypad, one or more buttons, a peripheral pointing device, a touchscreen, a voice recognition module, or another input mechanism that allows the user to navigate through a user interface of programmer 108 and provide input. Programmer 108 may further include a processor. The processor of programmer 108 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

In other examples, rather than being a handheld computing device or a dedicated computing device, programmer 108 may be a larger workstation or a separate application within another multi-function device. For example, the multi-function device may be a desktop computer, a notebook computer, a workstation computer, a cellular phone, or a personal digital assistant that can be configured by use of an application to simulate programmer 108. Alternatively, a notebook computer, tablet computer, or other personal computer may execute an application to function as programmer 108 (e.g., with a wireless adapter enabling the computer to communicate with device 100).

When programmer 108 is configured for use by the clinician, programmer 108 may be used to transmit initial programming information to device 100. This initial information may include hardware information for the fluid delivery system, such as the type of catheter 103, the position of catheter 103 within patient 101, the type of therapeutic agent delivered by device 100, a baseline orientation of at least a portion of device 100 relative to a reference point, therapy parameters of therapy programs stored within device 100 or within programmer 108, and any other information the clinician desires to program into device 100.

The clinician may use programmer 108 to program device 100 with one or more therapy programs that define the therapy delivered by device 100 to patient 101. During a programming session, the clinician may determine one or more therapy programs that provide effective therapy to patient 101. Patient 101 may provide feedback to the clinician as to the efficacy of a specific therapy program being evaluated or desired modifications to the therapy program.

Once the clinician has identified one or more therapy programs that may be beneficial to patient 101, patient 101 may continue the evaluation process and determine which of the therapy programs best alleviates the condition of or otherwise provides efficacious therapy to patient 101. Programmer 108 may assist the clinician in the creation/identification of therapy programs by providing a methodical system of identifying potentially beneficial therapy parameters.

A particular therapy program may set forth a number of therapy parameters, e.g., one or more doses of the therapeutic agent to be delivered to patient 101 by device 100 over one or more periods of time, patient-initiated bolus doses, durations, and time intervals between successive patient-initiated boluses (e.g., lock-out intervals), maximum doses that may be delivered over a given period of time (e.g., a maximum unit dose), and so forth. Device 100 may further include features that prevent delivering the therapeutic agent in a manner inconsistent with the therapy program (e.g., limiting the delivery according to safe delivery levels, or stopping the delivery altogether) and alert the clinician and/or patient 101 of any error conditions related to the delivery. A particular dose of the therapeutic agent provided to patient 101 over a particular period of time may convey to the clinician an indication of the probable efficacy of the agent and the possibility of side effects of the agent on patient 101. In general, a sufficient amount of the therapeutic agent should be administered in order to have a desired therapeutic effect, such as pain relief. However, the amount of the agent administered to patient 101 may be limited to a maximum amount, such as a maximum daily dose (e.g., corresponding to a maximum unit dose), in order to avoid potential side effects. As such, therapy parameters specified by the clinician via programmer 108 may be used to specify any of the above parameters and other parameters associated with delivery of a drug or other therapeutic agent to patient 101 by device 100.

In some cases, programmer 108 may be configured for use by patient 101. When configured as a patient programmer, programmer 108 may have limited functionality in order to prevent patient 101 from altering some aspects of the therapy program or functions of programmer 108 in a way that may be detrimental to patient's 101 health. In this manner, programmer 108 may only allow patient 101 to adjust certain therapy parameters or adjust a particular therapy parameter within a limited range. In some cases, programmer 108 may permit patient 101 to control device 100 to deliver a supplemental, patient-initiated bolus, if permitted by the applicable therapy program administered by device 100, e.g., if the delivery of the patient-initiated bolus would not violate a lockout interval or maximum unit dose of the therapy program. Programmer 108 may also provide status information to patient 101 regarding device 100 and programmer 108, such as an indication that therapy is being delivered, that a reservoir of device 101 needs to be refilled, or that a power source, e.g., a battery within programmer 108 or device 100, needs to be replaced or recharged.

Whether programmer 108 is configured for clinician or patient use, programmer 108 may communicate with device 100 or any other computing device via wireless communication link 107. Programmer 108, for example, may communicate with device 100 via wireless communication link 107 using radio frequency (RF) telemetry techniques. Programmer 108 may also communicate with another programmer or computing device via a wired or wireless connection using any of a variety of local communication techniques, such as wired communications according to the 802.3 (LAN) standard, or RF communication according to the 802.11 (WLAN) or Bluetooth specification sets, infrared (IR) communication according to the IRDA specification set, or other standard or proprietary telemetry protocols. Programmer 108 may also communicate with another programmer or computing device via exchange of removable storage media, such as magnetic or optical disks or semiconductor memory media (e.g., memory cards or "sticks"). Device 100 may also communicate with another computing device, such as another programmer or an intermediate device such as a home monitoring device. Device 100 may communicate with the other computing device wirelessly, similar to using wireless communications link 107 to communicate with programmer 108, or through a network. In one example, device 100 is connected wirelessly to an interim network device that is connected to the network in order to communicate with the other computing device.

In accordance with examples according to this disclosure, device 100 and/or programmer 108 may be configured to prevent or reduce the risk of improperly dosing patient 101 with the therapeutic agent in a case of software or hardware malfunction within the fluid delivery system comprising device 100 and programmer 108. For example, one or both of device 100 and programmer 108 may be configured to receive a total dose of the therapeutic agent to be delivered to patient 101 by device 100 over a total period of time, automatically divide the total dose into a plurality of unit doses, each of which is equal to a fraction of the total dose configured to be delivered to patient 101 by device 100 over a unit period of time equal to a fraction of the total period of time, and automatically program device 100 to deliver to patient 101 one of the plurality of unit doses over its respective unit period of time. Device 100 may be configured to deliver to patient 101 the one unit dose, and to not continue delivering the agent until receiving further instruction, e.g. being automatically programmed to deliver another unit dose. Additionally, in some examples, device 100 may be configured to stop delivering the therapeutic agent to patient 101 after the one unit dose has been delivered or when another condition is met, e.g., a delivery threshold is exceeded. In this manner, automatically dividing the total dose into the plurality of unit doses and automatically programming device 100 to deliver to patient 101 one of the plurality of unit doses at one time according to this disclosure may effectively limit the consequences of a software or hardware malfunction of a fluid delivery system comprising device 100 and programmer 108 by reducing the time over which the agent can be delivered to patient 101 according to a particular set of therapy parameters. In another example, programmer 108 may be in active communication with device 100 as the therapeutic agent is delivered to patient 101 and programmer 108 may be configured to remotely control a pump of device 100 to deliver the one unit dose and, in some examples, to stop delivering the agent to patient 101 after the one unit dose has been delivered, or when another condition is met, e.g., a delivery threshold is exceeded.

Figure 2:
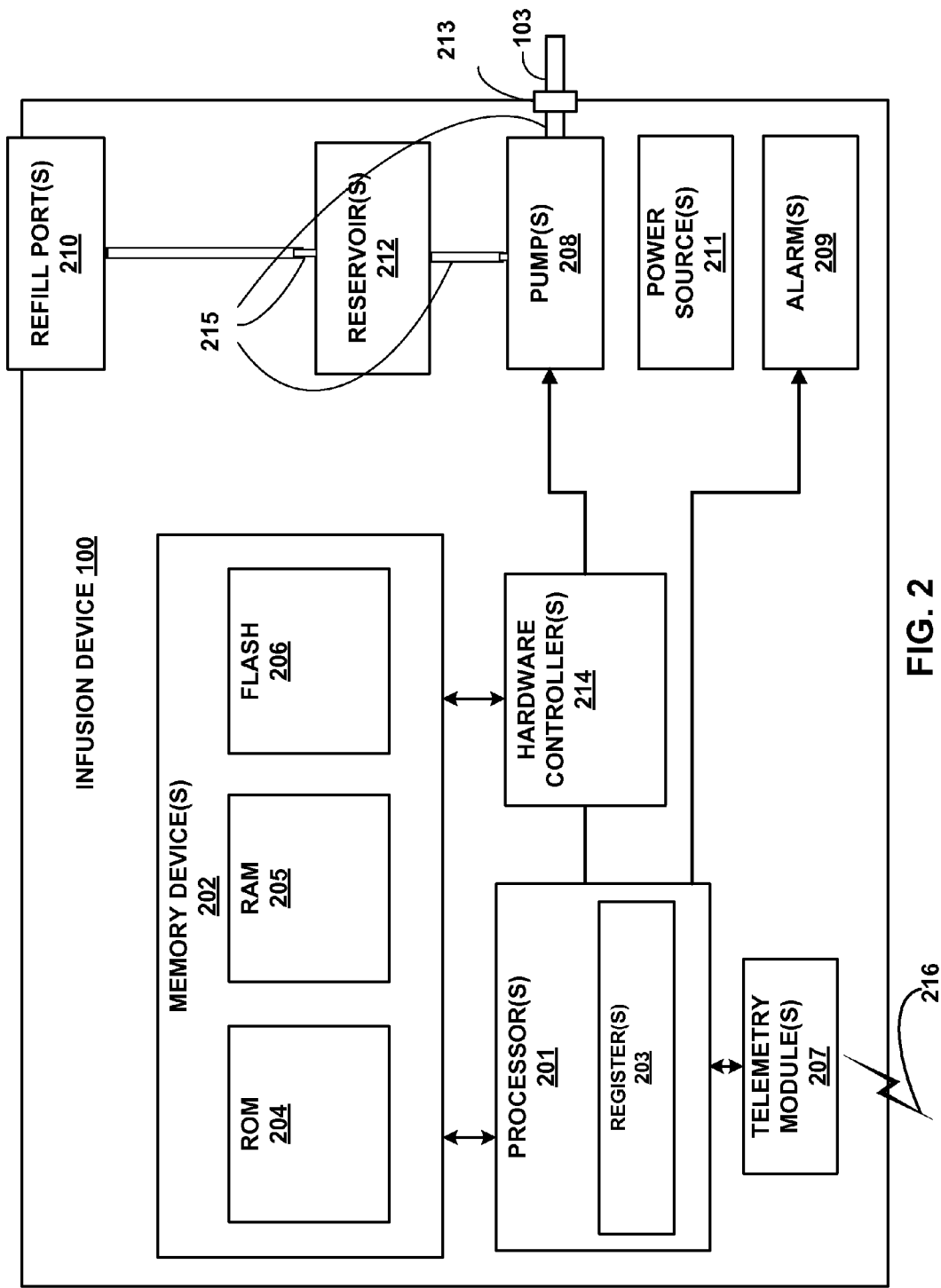
FIG. 2 is functional block diagram illustrating an example of an infusion device.

FIG. 2 is a functional block diagram illustrating components of an example of device 100 consistent with one or more aspects of this disclosure. As shown in FIG. 2, device 100 includes processor 201, memory device 202, telemetry module 207, alarm 209, power source 211, and hardware controller 214. Device 100 also includes refill port 210, reservoir 212, pump 208, catheter access port 213, and internal channels 215. In example device 100 of FIG. 2, memory device 202 includes read-only memory (ROM) 204, random access memory (RAM) 205, and FLASH memory 206. Processor 201 controls operation of pump 208 with the aid of hardware controller 214 and software instructions (now shown) stored in memory device 202. In one example, processor 201 is configured to execute the software instructions in order to control operation of device 100. The software instructions may define an infusion schedule that specifies a given amount of a therapeutic agent to be delivered to a target site within a patient from reservoir 212 via a catheter over a given period of time. For example, the infusion schedule may specify one or more doses of the therapeutic agent to be delivered to the patient by device 100 over one or more times. The software instructions may further define handling patient-initiated boluses, including specifying bolus doses, durations, and time intervals between successive boluses (e.g., lock-out intervals).

Pump 208 may be any mechanism fluidly coupled to reservoir 212 and catheter access port 213 that delivers a therapeutic agent from reservoir 212, through catheter access port 213 in some metered or otherwise monitored manner, e.g., to target site 105 within patient 101 via catheter 103, as depicted in FIG. 1. Examples of pump 208 include a peristaltic pump that uses rollers or other actuation devices to move fluid along a pump tube, and a piston pump, where a piston pushes fluid outward from the pump.

Refill port 210 may include a self-sealing injection port (not shown) fluidly coupled to reservoir 212. The self-sealing injection port may include a self-sealing membrane to prevent loss of a therapeutic agent delivered to reservoir 212 via refill port 210 when using an injection delivery system (e.g., a hypodermic needle) (not shown). After the injection delivery system penetrates the membrane of refill port 210 to refill reservoir 212 with the therapeutic agent and is removed from refill port 210, the membrane may seal shut to prevent loss of the agent through perforations in the membrane resulting from the injection delivery system.

Reservoir 212 may be any fluid vessel or cavity fluidly coupled to refill port 210 and pump 208, and capable of storing a therapeutic agent delivered to device 100 (and thereby stored in reservoir 212) via refill port 210.

Catheter access port 213 may be any coupling mechanism (e.g., a connector) for fluidly coupling pump 208 and a catheter (e.g., catheter 103 depicted in FIG. 1) for transporting a therapeutic agent from reservoir 212 to a target site within a patient. Internal channel 215 may include one or more segments of tubing or a series of cavities used to fluidly couple refill port 210, reservoir 212, pump 208, and catheter access port 213 to transport a therapeutic agent among these components and to a target site within a patient.

Processor 201 may include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry. As shown in FIG. 2, processor 201 may include one or more register(s) 203 (hereinafter "registers 203"), which may be used to execute software instructions and process data stored in memory device 202 and/or received by device 100 via telemetry module 207.

As discussed in further detail below, memory device 202 may be configured to store software instructions for execution by processor 201, including, but not limited to, instructions relating to firmware of device 100, therapy programs defining delivery of a therapeutic agent to a patient, and delivery limits. Memory device 202 may further store data, such as information related to device 100, patient information, and any other information regarding therapy of the patient. In the example shown in FIG. 2, memory device 202 includes ROM 204, RAM 205, and FLASH memory 206. Memory device 202 may include separate memory portions for storing the instructions and data. For example, relatively static information such as software instructions (e.g., device firmware, therapy programs, and delivery limits) may be stored in ROM 204 and/or FLASH memory 206, while relatively dynamic data (e.g., program variables and intermediate data) may be stored in RAM 205. Multiple copies of each of the foregoing types of information may be stored in different memory portions within memory device 202 for redundancy or backup of the information.

In accordance with examples according to this disclosure, processor 201 of device 100, alone or in conjunction with a processor or another component of programmer 108, may be configured to prevent or reduce the risk of improperly dosing patient 101 with the therapeutic agent in a case of software or hardware malfunction within the fluid delivery system comprising device 100 and programmer 108. For example, processor 201 may be configured to execute instructions stored in memory device 202 to receive a total dose of the therapeutic agent to be delivered to patient 101 by device 100 over a total period of time, automatically divide the total dose into a plurality of unit doses, each of which is equal to a fraction of the total dose configured to be delivered to patient 101 by device 100 over a unit period of time equal to a fraction of the total period of time, and automatically program device 100 to deliver to patient 101 one of the plurality of unit doses over its respective unit period of time. Processor 201, in conjunction with hardware controller 214, may be configured to control pump 208 to deliver the one unit dose to patient 101 via catheter 103, and to not continue delivering the agent until receiving further instruction, e.g. being automatically programmed to deliver another unit dose. Additionally, in some examples, processor 201 may be configured to stop delivering the therapeutic agent to patient 101 after the one unit dose has been delivered or when another condition is met, e.g., a delivery threshold is exceeded. In this manner, processor 201 automatically dividing the total dose into the plurality of unit doses and automatically programming device 100 to deliver to patient 101 one of the plurality of unit doses at one time according to this disclosure may effectively limit the consequences of a software or hardware malfunction of a fluid delivery system comprising device 100 and programmer 108 by reducing the time over which the agent can be delivered to patient 101 according to a particular set of therapy parameters. In another example, a processor or another component of programmer 108 may be in active communication with device 100 as the therapeutic agent is delivered to patient 101 and may be configured to remotely control, via hardware controller 214, pump 208 of device 100 to deliver the one unit dose and, in some examples, to stop delivering the agent to patient 101 after the one unit dose has been delivered, or when another condition is met, e.g., a delivery threshold is exceeded.

Hardware controller 214 may be configured to directly control one or more actuating devices (not shown) of pump 208. Hardware controller 214 may receive instructions regarding delivery of a therapeutic agent to a patient from processor 201, such as one or more doses of the therapeutic agent to be delivered to the patient by device 100 over one or more times corresponding to an infusion schedule stored in memory device 202, and control pump 208 accordingly. For example, if an infusion schedule stored in memory device 202, described in more detail below, or a patient-initiated bolus request received via telemetry module 207, dictates that at a particular point in time, device 100 should deliver a particular dose of the therapeutic agent to the patient over a particular period of time, processor 201 instructs hardware controller 214 to provide the particular dose over the particular period of time, and hardware controller 214 causes the one or more actuating devices of pump 208, such as rollers in a peristaltic pump or a piston in a piston pump, to be actuated in a manner that will provide the particular dose over the particular period of time. Additionally, as explained above, in examples according to this disclosure, processor 201 may be configured to automatically divide the total dose from the infusion schedule or bolus, or other source, into a plurality of unit doses, each of which is equal to a fraction of the total dose configured to be delivered to patient 101 by device 100 over a unit period of time equal to a fraction of the total period of time, and automatically instruct hardware controller 214 to cause pump 208 to deliver to patient 101 one of the unit doses over one unit period of time. Furthermore, hardware controller 214, alone or in conjunction with processor 201, may be configured to stop delivering the therapeutic agent to patient 101 after the one unit dose has been delivered, or when another condition is met, e.g., a delivery threshold is exceeded.

Hardware controller 214 may include one or more processors (not shown), including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "controller" may generally refer to any of the foregoing logic circuitry, alone or in combination with other logic circuitry, or any other equivalent circuitry.

Hardware controller 214 may also include a memory (not shown) that stores parameters associated with control of pump 208 (e.g., trim parameters, such as voltage references and bias currents), as well as parameters related to the delivery of the therapeutic agent to patient 101, including delivery limits, as described in further detail below. The memory may include any volatile or non-volatile media, such as ROM, RAM, electrically erasable programmable ROM (EEPROM), non-volatile RAM (NVRAM), FLASH memory, hardware registers, and the like. Hardware controller 214 may also include power circuitry (e.g., power transistors, drivers) (not shown) used to control the one or more actuating devices of pump 208, such as electromechanical transducers (e.g., peristaltic pump motors, piston solenoids) and the associated mechanical hardware (e.g., rollers in a peristaltic pump, and a piston in a piston pump).

Power source 211 delivers operating power to various components of device 100, including, but not limited to processor 201, memory device 202, hardware controller 214, pump 208, telemetry module 207, and alarm 209. Power source 211 may include a small rechargeable or non-rechargeable battery or other storage element and a power generation circuit to produce the operating power. In the case of a rechargeable battery, recharging may be accomplished through proximal inductive interaction between an external charger and an inductive charging coil (not shown) within device 100. In some examples, power requirements may be small enough to allow device 100 to utilize patient motion to generate the operating power using a kinetic energy-scavenging device to trickle-charge a rechargeable battery or a storage capacitor. In other examples, traditional batteries may be used for a limited period of time. As a further alternative, an external inductive power supply may be used to transcutaneously power device 100 whenever measurements of operation of device 100 are needed or desired.

As further shown in FIG. 2, device 100 may also include alarm 209 used to alert a clinician and/or patient of a condition within device 100, such as detection of an error condition while delivering a therapeutic agent to the patient according to an infusion schedule or a patient-initiated bolus request. As described in more detail below, alarm 209 may be used to indicate that the delivery of the agent to the patient according to the infusion schedule or bolus request has exceeded one or more threshold values, including, e.g., a maximum unit dose. Alarm 209 may be any device operable to draw the attention of the clinician and/or patient, such as an audible alarm (e.g., a piezoelectric speaker) that is heard by the clinician and/or patient, a vibrational alarm (e.g., a vibration motor), or an electrical stimulus alarm (e.g., a subcutaneous "tickle" electrode) that is felt by the patient, or a signal sent by device 100 to another device, such as an external computing device (e.g., programmer 108 depicted in FIG. 1).

Telemetry module 207 in device 100, along with a telemetry module (not shown) of an external programmer (e.g., programmer 108 depicted in FIG. 1), provide communication between device 100 and the programmer using communication link 216. Communication between the telemetry module of the programmer with telemetry module 207 may be accomplished by any communication mechanism, such as local wireless communication techniques including, but not limited to, RF communication according to the 802.11 (WLAN) or Bluetooth specification sets, infrared (IR) communication according to the IRDA specification set, or other standard or proprietary telemetry protocols. In addition, telemetry module 207 may communicate with the programmer via proximal inductive interaction of device 100 with the programmer. Processor 201, using instructions stored in memory device 202, may control telemetry module 207 to send information from device 100 and receive information by device 100.

Figure 3:
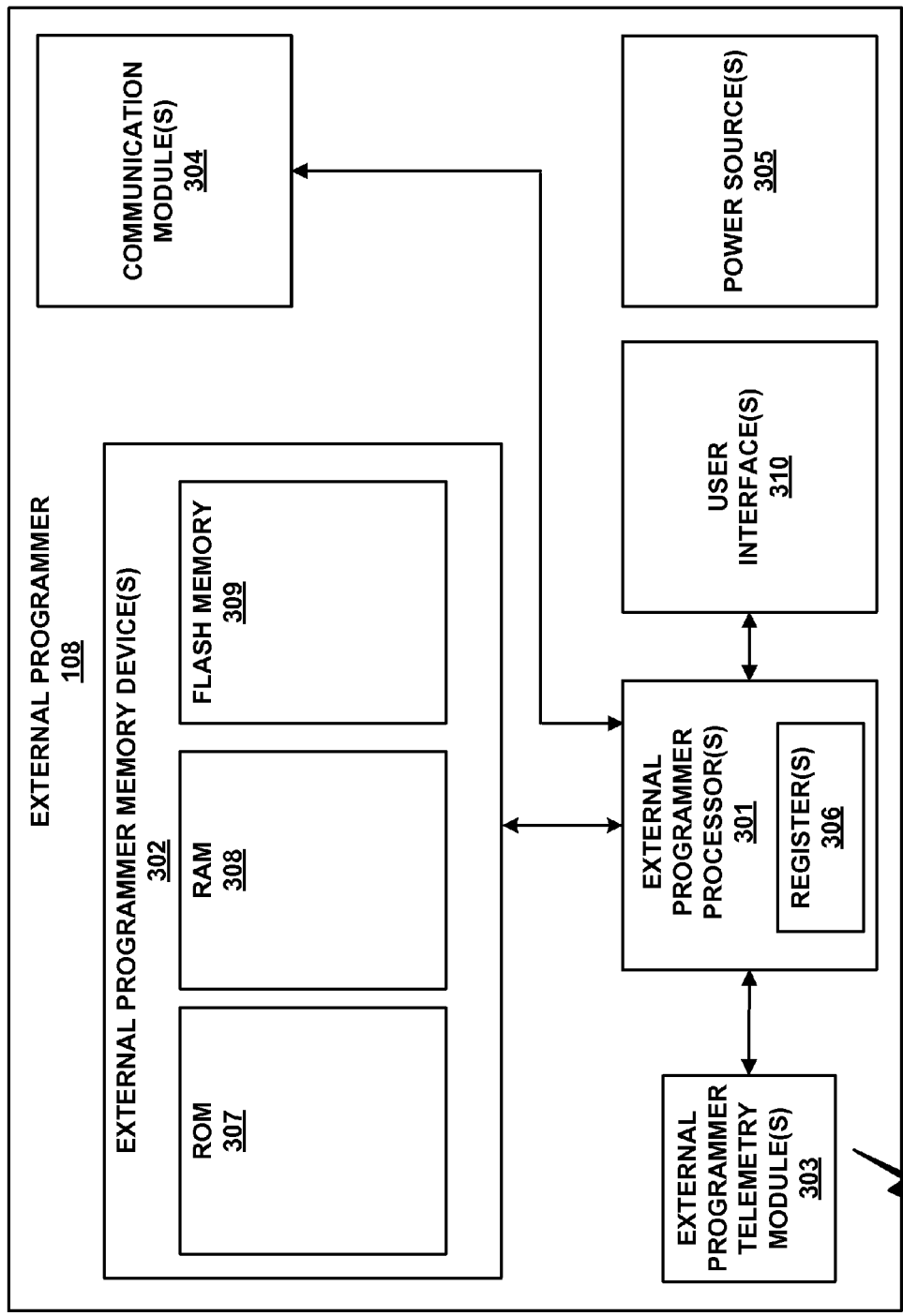
FIG. 3 is a functional block diagram illustrating an example of an external programmer configured to operate in conjunction with an infusion device.

FIG. 3 is a functional block diagram illustrating components of an example of programmer 108 consistent with one or more aspects of this disclosure. As shown in FIG. 3, programmer 108 includes processor 301, memory device 302, user interface 310, communication module 304, telemetry module 303, and power source 305. Processor 301 controls operation of programmer 108 with the aid of software instructions stored in memory device 302. In one example, processor 301 is configured to execute the software instructions in order to control operation of programmer 108. Additionally, the software instructions may define an infusion schedule that specifies one or more doses of a therapeutic agent to be delivered to a patient, e.g., patient 101 depicted in FIG. 1, by an infusion device, e.g., device 100 depicted in FIG. 2, over one or more times, as discussed above with reference to FIG. 2. As also discussed above with reference to FIG. 2, the software instructions may further define handling patient-initiated boluses, including specifying bolus doses, durations, and time intervals between successive boluses (e.g., lock-out intervals).

Processor 301 may include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry. processor 301 may further include one or more register(s) 306 (hereinafter "programmer registers 306"), which may be used to execute software instructions and process data stored in memory device 302 and received by programmer 108 via communication module 304.

Memory device 302 may include any volatile or non-volatile media, including, e.g., ROM, EEPROM, RAM, NVRAM, FLASH memory, and the like. As discussed in further detail below, memory device 302 may be configured to store software instructions for execution by processor 301, including, but not limited to instructions relating to firmware of programmer 108, therapy programs defining delivery of a therapeutic agent to a patient, and delivery limits. Memory device 302 may further store data, such as information related to programmer 108, patient information, and any other information regarding therapy of the patient. In the example shown in FIG. 3, memory device 302 includes a ROM 307, a RAM 308, and a FLASH memory 309. Memory device 302 may include separate memory portions for storing the instructions and data, as described above with reference to FIG. 2. For example, relatively static information such as software instructions (e.g., programmer firmware, therapy programs, and delivery limits) may be stored on ROM 307 and/or FLASH memory 309, while relatively dynamic data (e.g., program variables and intermediate data) may be stored in RAM 308. Multiple copies of each of the foregoing types of information may be stored in different memory portions within memory device 302 for redundancy or backup of the information.

In accordance with examples according to this disclosure, processor 301 of programmer 108, alone or in conjunction with processor 201 or another component of device 100, may be configured to prevent or reduce the risk of improperly dosing patient 101 with the therapeutic agent in a case of software or hardware malfunction within the fluid delivery system comprising device 100 and programmer 108. For example, processor 301 may be configured to execute instructions stored in memory device 302 to receive a total dose of the therapeutic agent to be delivered to patient 101 by device 100 over a total period of time, automatically divide the total dose into a plurality of unit doses, each of which is equal to a fraction of the total dose configured to be delivered to patient 101 by device 100 over a unit period of time equal to a fraction of the total period of time, and automatically program device 100 to deliver to patient 101 one of the plurality of unit doses over its respective unit period of time. Processor 301 may communicate the plurality of unit doses to device 100, e.g., for storage in memory device 202, via telemetry module 303. Device 100, e.g., using processor 201 in conjunction with hardware controller 214, may control pump 208 to deliver the one unit dose to patient 101 via catheter 103, and to not continue delivering the agent until receiving further instruction, e.g. being automatically programmed to deliver another unit dose by processor 301 of programmer 108. Additionally, in some examples, processor 201 may be configured to stop delivering the therapeutic agent to patient 101 after the one unit dose has been delivered or when another condition is met, e.g., a delivery threshold is exceeded. In this manner, processor 301 automatically dividing the total dose into the plurality of unit doses and automatically programming device 100 to deliver to patient 101 one of the plurality of unit doses at one time according to this disclosure may effectively limit the consequences of a software or hardware malfunction of a fluid delivery system comprising device 100 and programmer 108 by reducing the time over which the agent can be delivered to patient 101 according to a particular set of therapy parameters. In another example, processor 301 may be in active communication with device 100 as the therapeutic agent is delivered to patient 101 and may be configured to remotely control, via hardware controller 214, pump 208 of device 100 to deliver the one unit dose and, in some examples, to stop delivering the agent to patient 101 after the one unit dose has been delivered, or when another condition is met, e.g., a delivery threshold is exceeded.

User interface 310 may include hardware and/or software components of programmer 108 configured to receive and/or process input from a user, e.g., from a clinician and/or a patient. For example, user interface 310 may process user input indicating a desired therapy program or modification of an existing therapy program. In one example, user interface 310 is configured to receive from the user an indication of one or more doses of a therapeutic agent to be delivered to a patient by an infusion device, e.g., device 100 depicted in FIG. 2, over one or more times, as part of creating a therapy program or modifying an existing therapy program, or as part of a user-initiated bolus request. In addition, user interface 310 may be configured to receive from the user indications of delivery limits in the form of threshold values, e.g., a maximum unit dose. Examples of user input that may be received by user interface 310 include tactile button input, e.g., using one or more discrete buttons or a keyboard/keypad positioned on a surface of programmer 108 or a coupled peripheral device, touch-sense input, e.g., using a touchscreen positioned over a display or other surface of programmer 108 or peripheral device, voice command input, e.g., using a voice recognition module of programmer 108, electronic input, e.g., using a separate communicatively coupled computing device, such as a personal computer, and/or any other form of user input configured to indicate a desired therapy program, modification to an existing therapy program, a user-initiated bolus request, and/or delivery limits indicated by the user.

Communication module 304 may include any hardware and/or software components configured to enable programmer 108 to communicate with one or more devices (not shown) other than, e.g., device 100 depicted in FIG. 2. For example, communication module 304 may include any hardware and/or software components configured to enable programmer 108 to communicate with a computing device (e.g., a desktop computer, notebook computer, workstation computer, and the like) or another programmer via a wired or wireless connection using any of a variety of local communication techniques, such as wired communications according to the 802.3 (LAN) standard, or RF communication according to the 802.11 (WLAN) or Bluetooth specification sets, infrared (IR) communication according to the IRDA specification set, or other standard or proprietary telemetry protocols. Programmer 108 may also communicate with the computing device or programmer via exchange of removable storage media, such as magnetic or optical disks or semiconductor memory media (e.g., memory cards or "sticks"). Programmer 108 may also communicate with another computing device, such as an intermediate device, such as a home monitoring device, using any of the above communication techniques.

Telemetry module 303 and a telemetry module of an infusion device, e.g., telemetry module 207 of device 100 depicted in FIG. 2, may be configured to provide communication between programmer 108 and the infusion device using communication link 311. Communication between telemetry module 303 and the telemetry module of the infusion device may be accomplished by any communication mechanism, such as local wireless communication techniques including, but not limited to, RF communication according to the 802.11 (WLAN) or Bluetooth specification sets, infrared (IR) communication according to the IRDA specification set, or other standard or proprietary telemetry protocols. In addition, telemetry module 303 may communicate with the telemetry module via proximal inductive interaction of programmer 108 with the infusion device. Processor 301, using instructions stored in memory device 302, may control telemetry module 303 to send information to the infusion device and receive information from the infusion device.

Power source 305 delivers operating power to various components of programmer 108, including, but not limited to processor 301, memory device 302, user interface 310, communication module 304, and telemetry module 303. Power source 305 may include an off-line power source (e.g., AC power adapter) or rechargeable or non-rechargeable battery or other storage element, and a power generation circuit used to produce the operating power. In the case of a rechargeable battery, recharging may be accomplished through direct conduction or proximal inductive interaction between an external charger and an inductive charging coil (not shown) within device 300 (e.g., a charging dock). In other examples, traditional batteries may be used for a limited period of time.

The following discussion describes generally the configuration and arrangement of memory devices 202 and 302 of device 100 and programmer 108, respectively, and a memory internal to hardware controller 214, in accordance with the examples according to this disclosure. The function of memory devices 202 and 302 and the memory internal to hardware controller 214 in the context of preventing or reducing the risk of improperly dosing patient 101 with the therapeutic agent in a case of software or hardware malfunction within the fluid delivery system comprising device 100 and programmer 108 is described below with reference to the example method of FIG. 4. The following discussion is meant to be illustrative only, and, in other examples according to this disclosure, device 100 and programmer 108 may include a different number and type of memory device components, and may allocate storage of data, e.g., firmware, therapy programs, and delivery limits, differently than described below.

Referring back to FIG. 2, memory device 202 may contain ROM 204, RAM 205, and FLASH 206 memory components. In one example of FIG. 2, FLASH 206 may include device 100 firmware, one or more therapy programs, and delivery limits received by device 100 using telemetry module 207. RAM 205 may include redundant device 100 firmware, one or more therapy programs, and delivery limits, as well as locations for storing program variables and intermediate data. Finally, ROM 204 may include static device 100 firmware and delivery limits. Device 100 firmware, one or more therapy programs, and delivery limits may be stored in multiple components of memory device 202 as shown for redundancy or backup of the information, as well as for execution of associated software instructions by processor 201 and data manipulation. In other examples consistent with one or more aspects of this disclosure, these data may be stored differently within the ROM 204, RAM 205, and FLASH 206 memory components of memory device 202.

In another example, one or more components of memory device 202 may comprise a locked memory (e.g., also referred to as a "locked register"), wherein storing data in the locked memory requires writing a predetermined data value to a first location in the locked memory to unlock a second, non-contiguous, different location in the locked memory for a predetermined period of time, and subsequently storing, within the predetermined period of time, data in the second location. In this manner, inadvertent memory "writes" and other unintended manipulation of the contents of the locked memory are prevented or limited, thereby improving integrity of the data stored in the locked memory.

In still another example, an error-detection check, such as a cyclic redundancy check (CRC), may be provided to check for data corruption or other errors within the data stored in memory device 202. In one example, one or more CRC values (not shown) corresponding to device 100 firmware, one or more therapy programs, and/or delivery limits may be stored in FLASH 206 and/or RAM 205 to check for data corruption or other errors in these data. In one example, each CRC value may be stored along with its corresponding data, e.g., the data with which the CRC value will be used to check for corruption or other errors in the data. In another example, all CRC values may be stored together in a designated memory location, e.g., within FLASH 206 and/or RAM 205 separately from their corresponding data. Processor 201 may be configured to determine, using the one or more CRC values, whether data corruption or other errors within the data exist that prevent the continued use of the one or more therapy programs and/or delivery limits without unnecessary risk to a patient, and, upon determining the existence of such data corruption or errors, to cease using these data, to alert a clinician and/or patient of the data corruption or errors, and/or to request that the data be re-entered by the clinician and/or patient and re-transmitted to device 100.

Additionally, a memory internal to hardware controller 214 may also include a locked memory portion, and an error-detection check, such as a CRC, may be provided to check for data corruption or other errors within data stored in the memory, in the same or substantially similar manner as described above with reference to memory device 202.

Referring back to FIG. 3, memory device 302 may include ROM 307, RAM 308, and FLASH 309 memory components. In one example of FIG. 3, FLASH 309 may include programmer 108 firmware, one or more therapy programs, and delivery limits received by programmer 108 using communication module 304, user interface 310, and/or telemetry module 303. RAM 308 may include redundant one or more therapy programs, delivery limits, as well as locations for storing program variables and intermediate data. Finally, ROM 307 may include static programmer 108 firmware and delivery limits. Programmer 108 firmware, one or more therapy programs, and delivery limits may be stored in multiple components of memory device 302 as shown for redundancy or backup of the information, as well as for execution of associated software instructions by processor 301 and data manipulation. In other examples consistent with one or more aspects of this disclosure, these data may be stored differently within the ROM 307, RAM 308, and FLASH 309 memory components of memory device 302.

Additionally, one or more components of memory device 302 may comprise a locked memory, and an error-detection check, such as a cyclic redundancy check (CRC), may also be provided in order to check for data corruption or other errors within programmer 108 firmware, one or more therapy programs, and/or delivery limits stored in memory device 302, in the same or substantially similar manner as described above with reference to the example of FIG. 2.

Figure 4:
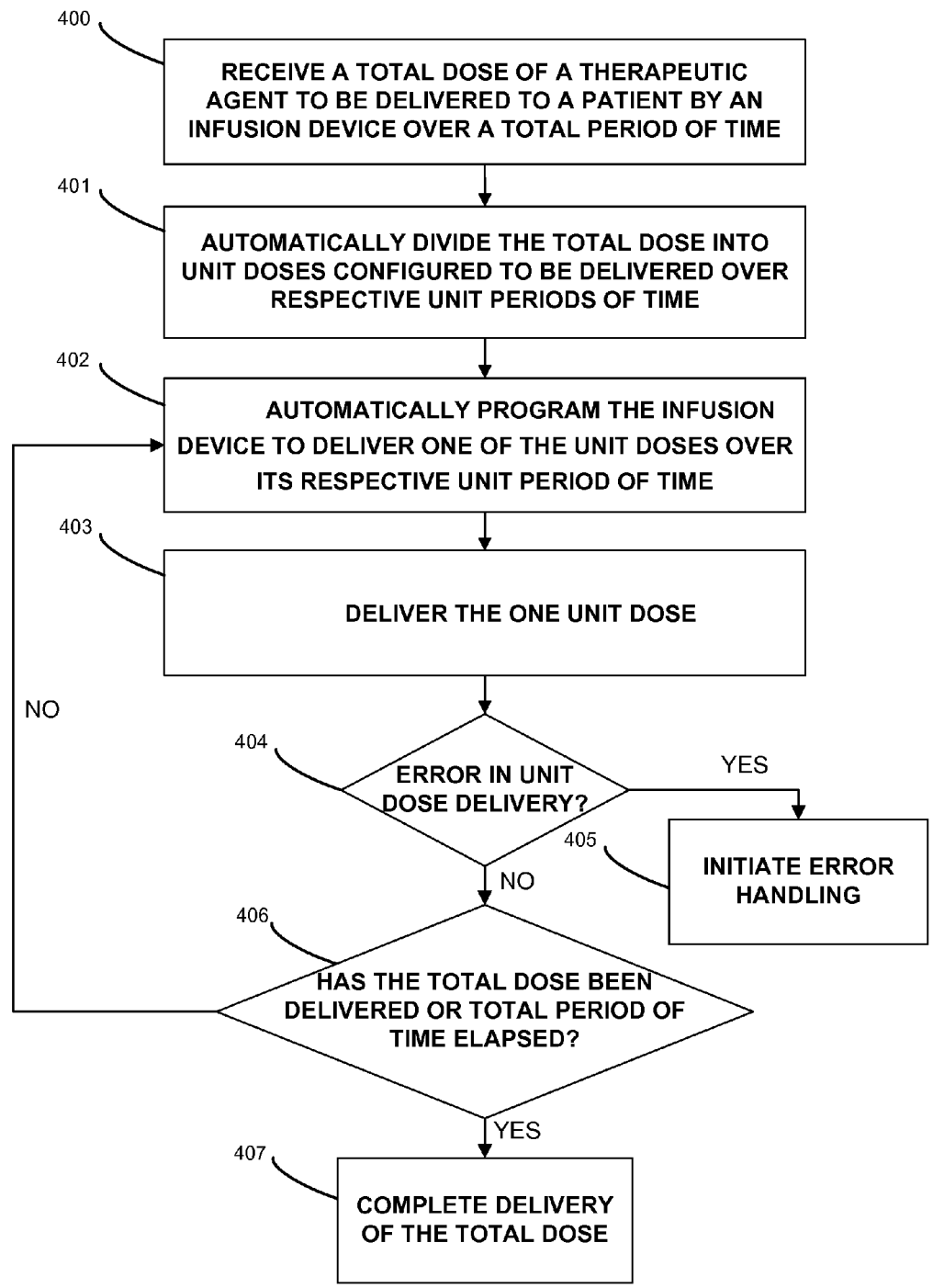
FIG. 4 is a flow diagram illustrating an example of a method according to this disclosure.

FIG. 4 is a flow diagram illustrating techniques of operating a fluid delivery system consistent with one or more aspects of this disclosure. In particular, FIG. 4 illustrates examples for preventing or reducing the risk of improperly dosing a patient with a therapeutic agent in the case of software or hardware malfunction of the fluid delivery system. The example method of FIG. 4 includes receiving a total dose of a therapeutic agent to be delivered to a patient by an infusion device over a total period of time (400); automatically dividing the total dose into a plurality of unit doses, each of which is equal to a fraction of the total dose configured to be delivered to the patient by the infusion device over a unit period of time equal to a fraction of the total period of time (401); automatically programming the infusion device to deliver to the patient one of the plurality of unit doses over its respective unit period of time (402); delivering to the patient, by the infusion device, the one unit dose (403); determining whether an error has occurred in delivering the one unit dose to the patient (404); initiating error handling in an event that an error has occurred in delivering the one unit dose to the patient (405); determining whether the total dose has been delivered, or the total period of time has elapsed (406); and completing the delivery of the total dose to the patient by the infusion device (407).

The example method of FIG. 4 includes receiving a total dose of a therapeutic agent to be delivered to a patient by an infusion device over a total period of time (400). Receiving the total dose may be performed by processor 301 of programmer 108, in conjunction with software instructions stored in memory device 302, processor 201 of device 100, in conjunction with software instructions stored in memory device 202, or both. In one example, one or more therapy programs are provided to processor 301 of programmer 108 by a clinician and/or patient 101 or another computing device using communication module 304, user interface 310, and/or telemetry module 303. The therapy programs include one or more infusion schedules specifying one or more doses of the therapeutic agent to be delivered to patient 101 by device 100 over one or more times. Any dose in an infusion schedule or therapy program may constitute the total dose, which may be automatically divided into a plurality of unit doses in examples according to this disclosure. For example, in constant-rate or dose infusion schedules defining therapy delivery by device 100 to patient 101 over, e.g., hours, days, or weeks at a constant delivery rate or dose, the constant dose of the infusion schedule may be the total dose. In another example, the total dose may be any of a number of different doses that are defined in a time-varying infusion schedule that includes different doses to be delivered over different periods of times. In another example, the total dose may be the dose defined by a bolus, e.g. a patient-initiated bolus received via user interface 310 of programmer 108. In one example, processor 201 may receive the total dose from programmer 108 or another computing device using telemetry module 207.

The example method of FIG. 4 further includes automatically dividing the total dose into a plurality of unit doses (401). Once again, automatically dividing the total dose into a plurality of unit doses may be performed by processor 301 of programmer 108, in conjunction with software instructions stored in memory device 302, processor 201 of device 100, in conjunction with software instructions stored in memory device 202, or both. In one example, programmer 108, and, in particular, processor 301, may be configured to automatically divide the total dose into a plurality of unit doses, and transmit the plurality of unit doses from programmer 108 to device 100 via telemetry module 207 and telemetry module 303. As explained above with reference to FIG. 3, one or more therapy programs may be stored in memory device 302 of programmer 108. As explained above with reference to FIG. 2, redundant one or more therapy programs may be stored in memory device 202 of device 100. In one example, upon transmitting the plurality of unit doses from programmer 108 to device 100, the unit doses may be stored in memory device 202 of device 100.

In examples where automatically dividing the total dose into a plurality of unit doses is performed by programmer 108, or another external device, the manner in which the automatic division is performed may be specified by direct programming by a clinician and/or patient 101 (e.g., using user interface 310). In other examples, the division is performed without clinician and/or patient 101 intervention by an algorithm or program that automatically divides the total dose statically into default unit doses, e.g., default amounts, or adaptively based on parameters associated with the therapeutic agent, e.g., whether the therapeutic agent has risks associated with over- or under-infusion, and/or parameters specific to patient 101, e.g., patient 101 weight, body composition, and the infusion history of patient 101.

In one example, a clinician and/or patient 101 may enter therapy parameters to define an infusion schedule or a bolus request, including, e.g., one or more doses of the therapeutic agent to be delivered to patient 101 over one or more times, and specify how the total dose is to be automatically divided by programmer 108 or the external device. In another example, the clinician and/or patient 101 may enter the therapy parameters, as well as the therapeutic agent and/or patient 101 parameters to be used by programmer 108 or the external device to automatically generate the one or more total dose divisions, i.e. one or more values of the unit doses into which the total dose is divided. In one example, the clinician and/or patient 101 may choose from one or more total dose divisions generated by programmer 108 or the external device based on the therapeutic agent and/or patient 101 parameters, and/or other considerations.

In another example, automatically dividing the total dose may be performed by processor 201 of device 100. In this example, one or more therapy programs may be provided to device 100 using telemetry module 207 from programmer 108 via telemetry module 303 or from another computing device and stored in memory device 202. Additionally, one or more bolus requests may be received by device 100. The one or more therapy programs or bolus requests may specify one or more doses of the therapeutic agent to be delivered to patient 101 over one or more times. Device 100, and, in particular, processor 201, may be configured to automatically divide the total dose into a plurality of unit doses. As discussed above with reference to processor 301 of programmer 108, the manner in which the automatic division is performed by processor 201 may be specified by direct programming by a clinician and/or patient 101 (e.g., using user interface 310 of programmer 108 and included in the one or more therapy programs provided to device 100). In other examples, the division is performed without clinician and/or patient 101 intervention by an algorithm or program that automatically divides the total dose statically into default unit doses, or adaptively based on parameters associated with the therapeutic agent and/or patient 101 (e.g., also included in the one or more therapy programs provided to device 100).

Therapy may be varied based on time because patient's 101 activities and needs may change and cycle according to time. Whether executed by programmer 108 or device 100, automatically dividing the total dose into the plurality of unit doses (401) may include automatically dividing multiple doses into a plurality of unit doses. In one example, an infusion schedule may specify a number of different doses to be delivered to patient 101 over a number of periods of time, for the duration of a given total period of time. An infusion schedule defined in this manner may be referred to as a time-varying infusion schedule. In other examples, however, an infusion schedule commonly known as a continuous infusion schedule or a patient-initiated bolus may specify only a single dose to be delivered to patient 101 over a period of time.

Automatically dividing the total dose into the plurality of unit doses (401) in the context of a time-varying infusion schedule specifying one or more doses to be delivered to patient 101 over one or more times may include dividing each one of the doses into a plurality of unit doses. For example, a time-varying infusion schedule may define therapy on a given day and at a given time according to a first dose corresponding to 300 micro-liters of a therapeutic agent to be delivered to patient 101 over 1 hour. In such an example, programmer 108 or device 100 may be configured to divide the total dose of 300 micro-liters to be delivered over 1 hour into a plurality of smaller unit doses to be delivered over smaller unit periods of time, e.g., 60 unit doses of 5 micro-liters, each to be delivered over 1 minute, such that successively delivering one unit dose over one unit period of time for 1 hour results in delivering the total dose of 300 micro-liters. Therapy on other days and times defined by the time-varying infusion schedule may be treated in the same or substantially similar manner as described above. In the context of a continuous infusion schedule of a patient-initiated bolus, automatically dividing the total dose into the plurality of unit doses (401) includes automatically dividing the single dose specified by the infusion schedule or bolus into a plurality of unit doses, as discussed above with referenced to a time-varying infusion schedule.

In one example, the total dose specified by the infusion schedule or patient-initiated bolus may be defined, instead of as an amount of the therapeutic agent to be delivered to patient 101 over a period of time, e.g., 300 micro-liters over 1 hour, as a number of cycles of pump 208 of device 100 to be performed over the period of time. For example, a single cycle of pump 208 may deliver a known amount of the therapeutic agent to patient 101 via catheter 103. As such, a total dose corresponding to an amount of the therapeutic agent to be delivered to patient 101 over a period of time may be defined as a number of cycles to be performed by pump 208 over that period of time. For example, pump 208 of device 100 may include a cycle volume of 1 micro-liter. As such, in one example, a total dose of 300 micro-liters to be delivered over 1 hour may correspond to 300 cycles of pump 208 to be performed over 1 hour, and may be automatically divided into a plurality of smaller sets of pump cycles to be performed over a plurality of smaller unit periods of time, e.g., 5 pump cycles to be performed over 1 minute, such that successively performing one set of pump cycles over one unit period of time for 1 hour results in delivering the total dose of 300 micro-liters.

In addition to automatically dividing the total dose into the plurality of unit doses (401), the method of FIG. 4 includes automatically programming the infusion device to deliver to the patient the one unit dose over its respective unit period of time (402). Automatically programming the infusion device to deliver to the patient the one unit dose over its respective unit period of time (402) may be performed using a variety of methods. For example, with reference to the example of FIG. 2, automatically programming device 100 to deliver to patient 101 the one unit dose over its respective unit period of time may be performed by processor 201, in conjunction with software instructions stored in memory device 202, and/or hardware controller 214. In one example, processor 201 may retrieve the one unit dose from memory device 202 and/or receive the one unit dose via telemetry module 207, and program hardware controller 214 to control pump 208 to deliver the one unit dose. In another example, processor 201 may be programmed to directly control hardware controller 214 to control pump 208 to deliver the one unit dose. In another example, with reference to FIG. 3, wherein programmer 108 is in communication with device 100 via telemetry module 207 and telemetry module 303, processor 301 of programmer 108 may control processor 201 to program hardware controller 214 to control pump 208 to deliver the one unit dose. In other examples, processor 301 may program processor 201 to program or directly control hardware controller 214 to control pump 208 to deliver the one unit dose. Accordingly, automatically programming device 100 to deliver to patient 101 the one unit dose over its respective unit period of time may be performed using one or more components of programmer 108, device 100, or both.

In addition to automatically programming the infusion device to deliver to the patient the one unit dose over its respective unit period of time (402), the method of FIG. 4 includes delivering to the patient, by the infusion device, the one unit dose (403). Delivering to the patient, by the infusion device, the one unit dose (403) may be performed using a variety of methods. For example, with reference to the example of FIG. 2, delivering the one unit dose to patient 101 may be performed by processor 201, in conjunction with software instructions stored in memory device 202, hardware controller 214, and/or pump 208. In one example, processor 201 may retrieve the one unit dose from memory device 202 and/or receive the one unit dose via telemetry module 207 and directly control hardware controller 214 to control pump 208 to deliver the one unit dose. In another example, processor 201 may pre-load hardware controller 214 with a value corresponding to the one unit dose such that hardware controller 214 may control pump 208 to perform the delivery of the agent without further intervention from processor 201. In this example, hardware controller 214 may be configured to provide processor 201 feedback indicating completion of the delivery of the one unit dose. In another example, with reference to FIG. 3, wherein programmer 108 is in communication with device 100 via telemetry module 207 and telemetry module 303, processor 301 of programmer 108 may control processor 201 to directly control hardware controller 214, or directly control hardware controller 214, to control pump 208 to deliver the one unit dose. In other examples, processor 301 may control processor 201 to pre-load hardware controller 214, or directly pre-load hardware controller 214, with a value corresponding to the one unit dose such that hardware controller 214 may control pump 208 to perform the delivery of the agent without further intervention from processor 301 or processor 201. In the above example, hardware controller 214 may be configured to provide processor 301 and/or processor 201 feedback indicating completion of the delivery of the one unit dose.

In addition to delivering to the patient, by the infusion device, the one unit dose (403), the method of FIG. 4 includes determining whether an error has occurred in delivering the one unit dose to the patient (404) and initiating error handling in an event that an error has occurred in delivering the one unit dose to the patient (405). Errors for which the example method of FIG. 4 may check and determine the occurrence of include hardware errors, e.g. errors in hardware controller 214 controlling pump 208 of device 100 to deliver a therapeutic agent to patient 101, as well as software errors, e.g. errors in processor 201 instructing hardware controller 214 in the delivery of the agent. In one example, processor 201 and/or other components of device 100 or programmer 108, e.g. hardware controller 214, may be configured to monitor the delivery of therapeutic agent to patient 101 by hardware controller 214 and pump 208 and check for errors in the amount of the unit dose delivered, e.g. in terms of a number of cycles of pump 208, as well as the amount of time over which pump 208 delivers the unit dose, i.e. check that the actual time of delivery corresponds to the programmed unit time period. In one example, processor 201 or another component, e.g. hardware controller 214, may also be configured to monitor the time between cycles of pump 208 as a check against how the unit dose is delivered over the unit time, e.g. all of the dose delivered at the top of the unit time period or at the bottom or substantially evenly over the unit time period. In the event any errors occur, processor 201 of device 100 or processor 301 of programmer 108 may initiate a number of different error handling techniques, including triggering alarms to alert users, e.g. patient 101 to the error, as well as stopping delivery of the therapeutic agent to patient 101 before the total dose has been delivered or the total period of time has elapsed. Determining whether the error has occurred in delivering the one unit dose to the patient (404) and initiating error handling in an event that the error has occurred (405) may be performed using a variety of methods, as will be described in further detail below.

In addition to determining whether the error has occurred in delivering the one unit dose to the patient (404) and initiating error handling in an event that the error has occurred (405), the method of FIG. 4 includes determining whether the total dose has been delivered, or the total period of time has elapsed (406), and completing the delivery of the total dose to the patient by the infusion device (407). Determining whether the total dose has been delivered, or the total period of time has elapsed (406) may be performed using a variety of methods. For example, with reference to the examples of FIGS. 2 and 3, determining whether the total dose has been delivered, or the total period of time has elapsed (406) may be performed by processor 201, in conjunction with software instructions stored in memory device 202, processor 301, in conjunction with software instructions stored in memory device 302, or both. In one example, processor 201 and/or processor 301 may track the number of unit doses delivered to patient 101, e.g., using one or more counters in memory devices 202 and/or 302, registers 203 and/or 306, and/or other internal or external devices, and compare the number of unit doses delivered against the number of unit doses into which the total dose has been divided, or compare a sum of the unit doses delivered against the total dose. In another example, processor 201 and/or processor 301 may track the time that has elapsed during delivery of the unit doses using one or more counters as described above, and compare the time to the total period of time. In still another example, hardware controller 214 may track the number of unit doses delivered to patient 101 and/or the time that has elapsed during delivery of the unit doses, using one or more counters, in the same or substantially similar manner as described above with reference to processors 201 and 301.

In one example, the one or more counters may be implemented in registers 203 of processor 201 and/or in memory device 202 of device 100, e.g., in RAM 205. Tracking the number of unit doses that have been delivered and the time that has elapsed during delivery of the unit doses may be performed by incrementing the one or more counters by processor 201 executing one or more software instructions corresponding to an incrementing operation stored in memory device 202, e.g., contained within one or more therapy programs. In one example, the counters may be implemented entirely within registers 203, in which case the values contained within the counters may be incremented directly by processor 201. In another example, counters may be implemented in one or more locations in memory device 202, e.g., in RAM 205, in which case processor 201 may retrieve values contained within the memory locations into registers 203, increment the values within the registers as previously described, and store the resulting incremented values into their respective locations in memory device 202. In other examples, the counters may be implemented using one or more dedicated modules within processor 201 other than registers 203 (e.g., a processor timer/counter module), or one or more devices separate from processor 201 and memory device 202 (e.g., discrete logic counters), wherein processor 201 may control the one or more modules or devices to increment the counters. In some examples, the one or more counters may be implemented in a memory internal to hardware controller 214 and incremented directly by hardware controller 214. In other examples, the one or more of the counters may be implemented in programmer 108 in the same or substantially similar manner as described above with reference to implementing the counters in device 100. In such examples, incrementing the counters and comparing their contents against the total dose and the total period of time may include programmer 108 communicating with and receiving unit dose delivery indications from device 100, e.g., via telemetry modules 207 and 303.

Comparing the values stored in the counters may be performed by processor 201, in conjunction with software instructions stored in memory device 202, processor 301, in conjunction with software instructions stored in memory device 302, hardware controller 214, or using any combination of the above devices and components. In one example, processor 201 may be configured to execute software instructions corresponding to comparing the values stored in memory device 202, e.g., included within one or more therapy programs. In other examples, where the counters are implemented using one or more devices external to processor 201 and memory device 202, processor 201 may control the one or more external devices and/or additional devices to compare the values. In still other examples, processor 201 may retrieve the values from the one or more external devices and compare the values internally to processor 201. In other examples, processor 301 and/or hardware controller 214 may perform the comparison in the same or substantially similar manner as described above with reference to processor 201. In the examples where the comparison is performed by processor 301 onboard programmer 108, a result of the comparison may be transmitted to device 100, e.g., using telemetry module 207 and telemetry module 303 or other components, to be used by device 100 in delivering the therapeutic agent to patient 101.

Completing the delivery of the total dose to the patient by the infusion device (407) may correspond to stopping delivering the therapeutic agent to patient 101 once the total dose has been delivered in unit dose increments, and may be performed by processor 301, in conjunction with software instructions stored in memory device 302, processor 201, in conjunction with software instructions stored in memory device 202, hardware controller 214, and/or pump 208, using the techniques described above with reference to delivering to patient 101, by device 100, the one unit dose (403). In one example, processor 201 may directly control hardware controller 214 to stop pump 208 from delivering the therapeutic agent. In another example, processor 201 may pre-load hardware controller 214 with a value corresponding to pump 208 stopping delivery of the agent. In this example, hardware controller 214 may be configured to provide processor 201 feedback indicating stopping the delivery. In another example, with reference to FIG. 3, wherein programmer 108 is in communication with device 100 via telemetry module 207 and telemetry module 303, processor 301 of programmer 108 may control processor 201 to directly control hardware controller 214, or directly control hardware controller 214, to control pump 208 to stop delivering the therapeutic agent. In other examples, processor 301 may control processor 201 to pre-load hardware controller 214, or directly pre-load hardware controller 214, with a value corresponding to pump 208 stopping delivery of the agent. In the above example, hardware controller 214 may be configured to provide processor 301 and/or processor 201 feedback indicating stopping the delivery of the agent. In other examples, completing the delivery of the total dose to the patient by the infusion device (407) may be followed by subsequent delivery of additional programmed doses, automatically divided into and delivered in unit doses over unit periods of time.

In accordance with examples according to this disclosure, the techniques of the example method of FIG. 4 described thus far may prevent or reduce the risk of improperly dosing patient 101 with the therapeutic agent in a case of software or hardware malfunction within the fluid delivery system comprising device 100 and programmer 108. For example, one or both of device 100 and programmer 108 may be configured to receive a total dose of the therapeutic agent to be delivered to patient 101 by device 100 over a total period of time, automatically divide the total dose into a plurality of unit doses, each of which is equal to a fraction of the total dose configured to be delivered to patient 101 by device 100 over a unit period of time equal to a fraction of the total period of time, and automatically program device 100 to deliver to patient 101 one of the plurality of unit doses over its respective unit period of time. Device 100 may be further configured to deliver to patient 101 the one unit dose, and iteratively repeat the above process until the total dose has been delivered, or the total period of time has elapsed. In this manner, automatically dividing the total dose into the plurality of unit doses and automatically programming device 100 to deliver to patient 101 only one of the plurality of unit doses at one time according to this disclosure may effectively limit the consequences of a software or hardware malfunction of a fluid delivery system comprising device 100 and programmer 108 by reducing the time over which the agent can be delivered to patient 101 according to a particular set of therapy parameters. In another example, programmer 108 may be in active communication with device 100 as the therapeutic agent is delivered to patient 101 and programmer 108 may be configured to remotely control pump 208 of device 100 to deliver the one unit dose. In either of the above cases, in an event of a software or hardware malfunction of the fluid delivery system, the process of device 100 iteratively delivering unit doses over unit periods of time to patient 101 until the total dose has been delivered, or the total period of time has elapsed may be interrupted, thereby preventing or reducing the risk of improperly dosing patient 101 with the therapeutic agent. In the event that no error occurs in delivering a given unit dose to patient 101, e.g., device 100 successfully delivers the one unit dose without exceeding any delivery thresholds, as will be described in further detail below, device 100 may continue delivering therapy to patient 101 by essentially starting over and delivering therapy according to another one of the unit doses into which the total dose has been divided, and so forth. As such, device 100 may, in the event no error occurs, continue to deliver therapy in individual unit dose segments until the total dose is delivered.

Referring back to determining whether the error has occurred in delivering the one unit dose to the patient (404) and initiating error handling in the event that the error has occurred (405) included in the method of FIG. 4, in some examples, the risk of an overdose or underdose of the therapeutic agent to patient 101 may be further reduced by limiting the delivery of the agent to patient 101 according to one or more threshold values. For example, determining whether the error has occurred (404) may include determining whether the delivery of the therapeutic agent to patient 101 exceeds one or more such threshold values, and initiating the error handling (405) may include responding to the above determination to mitigate the determined condition, as described in further detail below.

One such threshold value may be a maximum unit dose. Accordingly, in one example, determining whether the error has occurred in delivering the one unit dose to the patient (404) may include comparing the one unit dose to a maximum unit dose threshold. The maximum unit dose threshold, which limits the delivery of the therapeutic agent to patient 101 by device 100, may be determined employing programmer 108, device 100, and/or another external computing device. For example, determining the maximum unit dose threshold may be performed by processor 301, in conjunction with software instructions stored in memory device 302, by another external computing device, by processor 201 of device 100, in conjunction with software instructions stored in memory device 202, or using any combination of the above devices and components.

In one example, processor 301 may be configured to execute software instructions stored in memory device 302 corresponding to determining the maximum unit dose threshold, and to transmit the maximum unit dose threshold, using telemetry module 303 and telemetry module 207, to device 100 to be stored in memory device 202. In another example, the external computing device may determine the maximum unit dose threshold and transmit the maximum unit dose threshold to device 100 via programmer 108. For example, the maximum unit dose threshold may be stored as data corresponding to delivery limits in one or both of FLASH 206 and RAM 205. The maximum unit dose threshold may be determined by processor 301 or the external computing device using parameters associated with a particular therapeutic agent, e.g., whether the agent has risks associated with over infusion, and/or parameters specific to patient 101, e.g., patient 101 weight, body composition, and the infusion history of patient 101. In another example, the determination of the maximum unit dose threshold based on therapeutic agent and/or patient 101 parameters may be executed, in whole or in part, by processor 201 of device 100, in conjunction with software instructions stored in memory device 202, wherein the parameters are provided to device 100 and stored in memory device 202. According to another example, the maximum unit dose threshold may be determined based on input via user interface 310 of programmer 108 by a clinician and/or patient 101 and then may be transmitted from programmer 108 to device 100. In other examples, the maximum unit dose threshold may be stored as data corresponding to delivery limits in one or both of FLASH 309 and RAM 308 in memory device 302 onboard programmer 108. In another example, the maximum unit dose threshold may be determined automatically, e.g. by processor 201 based on one or more infusion schedules and/or bolus requests. In one example, the maximum unit dose threshold may be defined as the dose specified by a continuous infusion schedule. In another example, the maximum unit dose may be defined as the largest of multiple doses specified by a time-varying infusion schedule. In either a continuous or time-varying infusion schedule example, the maximum unit dose may be defined to additionally include a dose corresponding to an incremental bolus request. For example, the maximum unit dose threshold may include a dose specified by an infusion schedule, e.g. the largest of multiple doses prescribed by a time-varying infusion schedule plus a dose specified by an incremental bolus request. In another example, the maximum unit dose threshold may be defined as a dose specified by an exclusive bolus request, in a similar manner as described above with reference to the example of a continuous infusion schedule. Generally speaking, in all of the above examples where the maximum unit dose threshold is determined automatically, e.g. by processor 201 based on one or more infusion schedules and/or bolus requests, the maximum dose automatically determined is divided accordingly to match the time-base of the one unit dose to be delivered to patient 101 by device 100, for the purposes of comparison to the one unit dose.

In one example, processor 201 or another component, e.g. processor 301 of programmer 108 may automatically increase the automatically determined maximum unit dose. For example, processor 201 may statically add a certain percentage increase, e.g. 20% to the automatically determined maximum unit dose based on user input, e.g. from a clinician, or may add a percentage to the maximum unit dose that is determined by processor 201 based on, e.g. the infusion schedule. Increasing the threshold maximum unit dose that processor 201 or another component automatically determines may provide increased flexibility in the operation of device 100 to deliver therapy to patient 101, e.g. in examples in which device 100 is configured to allow some accumulation of undelivered amounts of the unit dose between successive unit doses, as explained in more detail below.

Regardless of which devices or particular components are employed to determine the maximum unit dose threshold, and irrespective of where the maximum unit dose threshold is stored, the maximum unit dose threshold may be stored in a portion of memory, e.g., memory device 202, memory device 302, and/or a memory internal to hardware controller 214, comprising a locked memory, as described above with reference to FIGS. 2 and 3. As such, the maximum unit dose threshold may be prevented from being inadvertently erased or modified by unintended operations of processor 301, processor 201, or other components of the fluid delivery system.

Comparing the one unit dose to the maximum unit dose threshold may, generally speaking, be performed by processor 301, in conjunction with software instructions stored in memory device 302, by another external computing device, by processor 201, in conjunction with software instructions stored in memory device 202, by hardware controller 214, or using any combination of the above devices and components, using the same or substantially similar techniques described above with reference to determining whether the total dose has been delivered, or the total period of time has elapsed (406). In one example, the maximum unit dose threshold and the one unit dose into which the total dose has been divided are compared by processor 301 onboard programmer 108, or by the external computing device, after the total dose is automatically divided into the plurality of unit doses, but before the plurality of unit doses or the one unit dose is transmitted to device 100. In the event that the one dose is greater than the maximum unit dose threshold, programmer 108 or the external computing device may be configured to indicate that an error condition is present without ever transmitting the plurality of unit doses or the one unit dose to device 100.

In another example, processor 301 may be configured to execute software instructions stored in memory device 302 (e.g., included within one or more therapy programs) corresponding to comparing the one unit dose which device 100 is, or soon will be, delivering to the maximum unit dose threshold onboard programmer 108. In another example, the external computing device may perform the comparison. In the examples where the comparison is performed by processor 301 onboard programmer 108 or by the external computing device, a result of the comparison may be transmitted to device 100, e.g., using telemetry module 207 and telemetry module 303 or other components, to be used by device 100 in delivering the therapeutic agent to patient 101. In another example, processor 201 may be configured to execute software instructions stored in memory device 202 corresponding to comparing the one unit dose to the maximum unit dose threshold onboard device 100. In still another example, hardware controller 214 may compare the one unit dose to the maximum unit dose threshold, wherein hardware controller 214 retrieves the maximum unit dose threshold from memory device 202 or receives the maximum unit dose threshold from processor 201 or processor 301 (e.g., via telemetry modules 207 and 303 and processor 201), and compares the one unit dose to the maximum unit dose threshold. In another example, hardware controller 214 may store the maximum unit dose threshold in a memory internal to hardware controller 214 for the purposes of comparing the one unit dose to the maximum unit dose threshold.

Regardless of which devices or particular components are employed to execute the comparison between the one unit dose and the maximum unit dose threshold, initiating error handling in the event that the error has occurred (405) may include device 100 configured to deliver the therapeutic agent to patient 101 according to the one unit dose in the event the one unit dose is less than or equal to the maximum unit dose threshold, and to deliver the agent to patient 101 according to the maximum unit dose threshold, deliver the agent to patient 101 according to a therapeutically-safe unit dose, stop delivery of the agent to patient 101 altogether, and/or generate an alarm alerting the clinician and/or patient 101 of an error condition, in the event the one unit dose is greater than the maximum unit dose threshold.

Delivering the therapeutic agent to patient 101 according to the maximum unit dose threshold and the therapeutically-safe unit dose, and stopping the delivery of the agent to patient 101 may be performed by processor 301, in conjunction with software instructions stored in memory device 302, processor 201, in conjunction with software instructions stored in memory device 202, hardware controller 214, and/or pump 208, using the same or substantially similar techniques as those described above with reference to delivering to patient 101, by the device 100, the one unit dose (403). For example, one or both of processor 301 and processor 201 may retrieve the maximum unit dose threshold or the therapeutically-safe unit dose, e.g., stored as data corresponding to delivery limits in one or more of FLASH 206, FLASH 309, RAM 205, and RAM 308, and directly control or pre-load hardware controller 214 to control pump 208 to deliver the therapeutic agent to patient 101 according to the maximum unit dose threshold or the therapeutically-safe unit dose. In another example, hardware controller 214 may retrieve the maximum unit dose threshold or the therapeutically-safe unit dose from memory device 202, or receive the maximum unit dose threshold or the therapeutically-safe unit dose from processor 201 or processor 301 (e.g., via telemetry modules 207 and 303 and processor 201), and control pump 208 to deliver the therapeutic agent to patient 101 according to the maximum unit dose threshold or the therapeutically-safe unit dose. In another example, hardware controller 214 may store the maximum unit dose threshold and/or the therapeutically-safe unit dose in a memory internal to hardware controller 214 for the purposes of delivering the agent to patient 101 according to the maximum unit dose threshold or the therapeutically-safe unit dose. The therapeutically-safe unit dose may be determined using parameters associated with the therapeutic agent, e.g., whether the therapeutic agent has risks associated with over- or under-infusion, and/or parameters specific to patient 101, e.g., patient 101 weight, body composition, and the infusion history of patient 101. In one example, the therapeutically-safe unit dose may be a default or safe mode dose that represents a minimum amount of the agent to be delivered to patient 101 in the event of certain error conditions that prevent delivery according to the programmed unit doses. Stopping the delivery of the agent to patient 101 may be performed in the same or substantially the same manner as described above with reference to completing the delivery of the total dose to patient 101 by the infusion device (407).

Generating the alarm alerting the clinician and/or patient 101 of the error condition may be performed by processor 301, processor 201, hardware controller 214, and/or another external computing device associated with the fluid delivery system (e.g., a workstation computer), and may generally include audible, palpable, and/or visual feedback to alert the clinician and/or patient 101 of the error condition. In one example, an alarm indicating the error condition may include audible and/or visual alerts issued by programmer 108 or the external computing device, thereby alerting the clinician and/or patient 101 of the error condition. In another example, the alarm may include device 100 vibrating or emitting an audible sound or electrical tissue stimulation within the body of patient 101, thereby alerting patient 101 of the error condition. In still another example, processor 201 and/or hardware controller 214 may be configured to prompt programmer 108, e.g., using telemetry module 207 and telemetry module 303, or the external computing device, to alert the clinician and/or patient 101 using an audible, palpable, and/or visual alert. Other alarms may include text or graphical messages delivered to the clinician and/or patient 101 via a text message or e-mail system from programmer 108, the external computing device, or another electronic device communicatively coupled to device 100, programmer 108, and/or the external computing device.

Additional thresholds other than the maximum unit dose threshold may be employed to further prevent or reduce the risk of an overdose or underdose of the therapeutic agent to patient 101. In one example in which the total dose has been divided into a plurality of unit doses, and each unit dose is expressed as a set of cycles of pump 208 of device 100, the number of pump cycles in the one set of pump cycles according to which device 100 is programmed to deliver the therapeutic agent to patient 101 may be compared to a redundant number of pump cycles threshold. Additionally, in another example, a maximum time to complete all pump cycles may be employed alone, or in conjunction with, the redundant number of pump cycles threshold, as another check on proper delivery of the therapeutic agent to patient 101 to assure that the one set of pump cycles is delivered within a prescribed time. Accordingly, in one example, determining whether the error has occurred in delivering the one unit dose to the patient (404) may include comparing the number of pump cycles in the one set of pump cycles to a redundant number of pump cycles threshold. In another example, determining whether the error has occurred in delivering the one unit dose to the patient (404) may include comparing a time to deliver the one set of pump cycles to a maximum time to complete all pump cycles threshold.

In order to implement the redundant number of pump cycles threshold, device 100 and/or programmer 108 may employ a number of counters to track and compare the one set of pump cycles and the redundant number of pump cycles threshold as device 100 delivers the therapeutic agent to patient 101. In one example, two counters may be employed and loaded with values corresponding to the one set of pump cycles and the redundant number of pump cycles threshold, wherein the redundant number of pump cycles threshold equals to the number of pump cycles in the one set of pump cycles. As device 100 delivers the therapeutic agent to patient 101 according to the one set of pump cycles, device 100 and/or programmer 108 may be configured to decrement each of the two counters for each cycle of pump 208 using independent processes (e.g., corresponding to software instructions stored in different components of memory devices 202 or 302, or in different portions of one of the components) and continuously compare the values in each counter against one another. In the event the values in the two counters are found to be different, device 100 may deliver the therapeutic agent to patient 101 according to the redundant number of pump cycles threshold, deliver the therapeutic agent to patient 101 according to a therapeutically-safe number of pump cycles, stop delivery of the agent to patient 101 altogether, and/or generate an alarm alerting a clinician and/or patient 101 of an error condition. Delivering the therapeutic agent to patient 101 according to the redundant number of pump cycles threshold and the therapeutically-safe number of pump cycles may be performed in the same or substantially similar manner as delivering the agent to patient 101 according to the one set of pump cycles, e.g., by processor 301, in conjunction with software instructions stored in memory device 302, processor 201, in conjunction with software instructions stored in memory device 202, hardware controller 214, and/or pump 208, using the techniques described above with reference to delivering to patient 101, by device 100, the one unit dose (403). The therapeutically-safe number of pump cycles may be determined in the same or substantially similar manner as described above with reference to determining the therapeutically-safe unit dose, using parameters associated with the therapeutic agent, e.g., whether the therapeutic agent has risks associated with over- or under-infusion, and/or parameters specific to patient 101, e.g., patient 101 weight, body composition, and the infusion history of patient 101. In other examples, rather than continuously comparing the values in the two counters, device 100 and/or programmer 108 may stop delivery of the agent to patient 101 when either the counter corresponding to the one set of pump cycles reaches zero, or the counter corresponding to the redundant number of pump cycles reaches zero.

Implementing the two counters and comparison of the values in the two counters may be performed using the same or substantially similar techniques as described above with reference to determining whether the total dose has been delivered, or the total period of time has elapsed (406). For example, decrementing the two counters may be performed by processor 201 executing one or more software instructions corresponding to a decrementing operation stored in memory device 202, e.g., contained within one or more therapy programs. In other examples, the two counters may be implemented in a memory internal to hardware controller 214 and decremented directly by hardware controller 214. In still other examples, where the two counters are implemented in programmer 108, decrementing the counters and comparing their contents against one another may include programmer 108 communicating with and receiving unit dose delivery indications from device 100, e.g., via telemetry modules 207 and 303, and transmitting to device 100 a result of the comparison to be used by device 100 in delivering the therapeutic agent to patient 101. Additionally, the counter corresponding to the redundant number of pump cycles threshold may be implemented in a locked memory portion of a memory, as described above with reference to FIGS. 2 and 3.

Although the above examples have been described with reference to decrementing the two counters, in another example, the counters may start at zero and be incremented up from zero to the one set of pump cycles and the redundant number of pump cycles threshold. In such an example, device 100 and/or programmer 108 may be configured to compare the values in the two counters against one another, and to respond in the same or substantially similar manner as described above in the event the two values are different, or stop delivery of the agent to patient 101 when either of the two counters reaches its respective one set of pump cycles and redundant number of pump cycles threshold.

Additionally, in examples where the total dose has been divided into a plurality of unit doses, and each unit dose is expressed as a set of cycles of pump 208 of device 100, the number of pump cycles in the one set of pump cycles according to which device 100 is programmed to deliver the therapeutic agent to patient 101 may be a non-integer number. In such cases, the fractional portion of the non-integer number of pump cycles in the one set of pump cycles may be stored and carried over to a next set of pump cycles according to which device 100 is programmed to deliver the therapeutic agent to patient 101. The fractional portion may be added to a fractional portion of the next set of pump cycles, and so forth, until an integer number of pump cycles is accumulated from multiple fractional portions, upon which the integer number may be delivered along with a set of pump cycles corresponding to the unit period of time in which the integer number of pump cycles was accumulated. This may be performed for both of the two counters, as described above.

Furthermore, the fractional portions may be stored and accumulated in one or more counters, using the same or substantially similar techniques as described above with reference to determining whether the total dose has been delivered, or the total period of time has elapsed (406). For example, in cases where the one or more counters are implemented in registers 203 of processor 201 and/or in memory device 202 of device 100, e.g., in RAM 205, accumulating the fractional portions may be performed by adding the values contained within the one or more counters by processor 201 executing one or more software instructions corresponding to an adding operation stored in memory device 202, e.g., contained within one or more therapy programs. In one example, where the counters are implemented entirely within registers 203, the values contained within the counters may be added directly by processor 201. In another example, where the counters are implemented in one or more locations in memory device 202, e.g., in RAM 205, processor 201 may retrieve the counter values contained within the memory locations into registers 203, add the values within the registers as previously described, and store the resulting value in a designated location in memory device 202. In other examples, where the counters are implemented using one or more dedicated modules within processor 201 other than registers 203 (e.g., a processor timer/counter module), or one or more devices separate from processor 201 and memory device 202 (e.g., discrete logic counters), processor 201 may control the one or more modules or devices to add the counters. In some examples, the counters may be implemented in a memory internal to hardware controller 214 and added directly by hardware controller 214. In other examples, the counters may be implemented in programmer 108 in the same or substantially similar manner as described above with reference to implementing the counters in device 100. In such examples, adding the counters may include programmer 108 communicating with and transmitting to device 100, e.g., via telemetry modules 207 and 303, accumulated fractional portions (e.g., integer accumulated portions) to be used by device 100 in delivering the therapeutic agent to patient 101.

The maximum unit dose and redundant number of pump cycle thresholds described above may act as an additional level of protection against improperly dosing patient 101 with the therapeutic agent. These thresholds may provide protection against various hardware or software malfunctions of a fluid delivery system consistent with one or more aspects of this disclosure. In one example, a clinician prescribes an allowed maximum dose of the therapeutic agent to be delivered to patient 101 by device 100, which may be defined as a maximum amount of the agent to be delivered over a period of time, or a maximum number of cycles of pump 208 of device 100 to be performed over the period of time, as described above. The maximum dose may be automatically divided into a maximum unit dose threshold to match the time-base of the unit doses in the automatically divided plurality of unit doses, as also described above. Subsequently, the clinician or a different user may incorrectly program device 100 to specify a total dose of the agent to be delivered to patient 101 that is greater than the maximum dose. Alternatively, a software or hardware malfunction in one or more components of the fluid delivery system, as described above, may cause an incorrect total dose to be specified that is greater than the maximum dose. The determination that the specified dose exceeds the maximum dose may be made on a total dose or unit dose basis. In the above examples, device 100, programmer 108, and/or another external computing device may be configured to detect an error condition as a result of the specified incorrect total dose, and perform one or more of the following: deliver the maximum dose, deliver a therapeutically-safe dose, stop the delivery altogether, and/or generate an alarm alerting the clinician and/or patient 101 of the error condition.

In another example, a hardware malfunction within device 100 and/or programmer 108 results in the counter corresponding to the one set of pump cycles, as described above, not decrementing properly or at all. In such a case, device 100 and/or programmer 108 may include a redundant counter that is pre-loaded with a redundant number of pump cycles equal to the number of pump cycles in the one set of pump cycles along with the errant counter. Both counters are decremented, using independent processes, for each cycle performed by pump 208 and compared to one another. In the event that the values in the two counters are found to be different, device 100, programmer 108, and/or another external computing device may be configured to detect an error condition, and perform one or more of the following: deliver the redundant number of pump cycles, deliver a therapeutically-safe number of pump cycles, stop the delivery altogether, and/or generate an alarm alerting the clinician and/or patient 101 of the error condition. In other examples, rather than continuously comparing the values in the two counters, device 100, programmer 108, and/or another external computing device may stop delivery of the agent to patient 101 when either the counter corresponding to the one set of pump cycles reaches zero, or the counter corresponding to the redundant number of pump cycles reaches zero.

In the cases of software or hardware malfunction described above, storage of data by which therapy is configured to be delivered may be implemented in separate memory devices or portions of one memory device. For example, the one unit dose or the one set of pump cycles according to which device 100 is configured to deliver the therapeutic agent to patient 101 may be stored in one memory location, while one or more of the foregoing delivery thresholds, e.g., maximum unit dose and redundant number of pump cycles thresholds, may be stored in a different memory location. In one example, the one unit dose or the one set of pump cycles may be stored in a general portion of RAM 308 of memory device 302, while the maximum unit dose and/or redundant number of pump cycles thresholds may be stored as data corresponding to delivery limits in, e.g., a locked portion of RAM 308 or FLASH 309, such that a hardware malfunction in the general portion of RAM 308 may not affect operation of the locked portion of RAM 308 or FLASH 309. The same or similar allocation of data by which therapy is configured to be delivered may take place within memory device 202 onboard device 100. Additionally, the one unit dose or the one set of pump cycles may be stored in a general portion of a memory internal to hardware controller 214, while the maximum unit dose and/or redundant number of pump cycles thresholds may be stored in, e.g., a locked portion of the memory, wherein the general portion and the locked portion of the memory may be contained within a single memory device, or within different memory devices internal to hardware controller 214.

As discussed above, in addition to the maximum unit dose and redundant number of pump cycles thresholds, additional thresholds may be employed to control delivery of the therapeutic agent to patient 101 in accordance with this disclosure. For example, a maximum time to complete all cycles in the one set of pump cycles may be employed in examples according to this disclosure. The maximum time for all pump cycles threshold may be employed in the context of examples in which the total dose has been divided into a plurality of unit doses, and each unit dose is expressed as a set of cycles of pump 208 of device 100, independent of, or in conjunction with, the redundant number of pump cycles threshold.

The maximum time for all pump cycles threshold may be employed to prevent or reduce the risk that therapy is delivered too slowly to patient 101, which may be adverse to patient's 101 health, and may indicate a software or hardware malfunction within the fluid delivery system. For example, as described above, an infusion schedule may specify a dose of 300 micro-liters to be delivered over 1 hour and may be automatically divided into a plurality of unit doses, e.g., 60 doses of 5 micro-liters to be delivered over 1 minute. As also described above, each cycle of pump 208 of device 100 may correspond to delivering 1 micro-liter of the therapeutic agent to patient 101. Accordingly, the one set of pump cycles corresponding to the one unit dose includes 5 pump cycles to be delivered over 1 minute. In the above example, if the one set of pump cycles being delivered to patient 101 is compared against only the redundant number of pump cycles threshold, as described above, in an event of an error condition, there is a risk that device 100 may deliver a correct number of pump cycles specified by the one set of pump cycles, but violate the one minute delivery duration specified by the one set of pump cycles. Accordingly, device 100 may deliver the 5 cycles to patient 101 too slowly. In another example, processor 201, or, e.g. processor 301 of programmer 108 may instruct hardware controller 214 to deliver the unit dose in terms of pump cycles, but due to one of many conditions, such as, e.g. a hardware state machine error, heavier load on power source 211 of device 100 (e.g. because multiple high current devices such as telemetry module 207 may be on), hardware lock-up or in degradation for any reason, hardware controller 214 fails to deliver the number of pump cycles in the unit period of time. In such examples, the maximum time for all pump cycles threshold may be employed such that, if either the one set of pump cycles is delivered, or the maximum time for all pump cycles threshold is met before the one set of pump cycles is delivered, device 100, programmer 108, and/or another external device may stop delivering the therapeutic agent to patient 101. Device 100, programmer 108, and/or the external device may also take corrective actions beyond stopping delivery, such as generating an alarm to alert a clinician and/or patient 101 of the error condition.

In one example of employing the maximum time for all pump cycles threshold, one or more counters may be employed in a similar manner as described above with reference to the redundant number of pump cycles threshold. For example, one or more counters may be implemented in registers 203/306 of processor 201/301, in memory device 202/302, e.g., in RAM 205/308, in a memory internal to hardware controller 214, and/or in other internal or external devices, to determine a time elapsed as the therapeutic agent is delivered to patient 101 according to the one set of pump cycles. As the agent is delivered to patient 101, the counters may be incremented or decremented (e.g., if pre-loaded with the maximum time for all pump cycles threshold). If the counters, when initially cleared and subsequently incremented, reach the maximum time for all pump cycles threshold, or, when pre-loaded with the maximum time for all pump cycles threshold and decremented, reach zero before all cycles in the one set of pump cycles have been performed, indicating an error condition, device 100, programmer 108, and/or the external device may be configured to stop delivering the therapeutic agent to patient 101 and/or generate an alarm alerting a clinician and/or patient 101 of the error condition. If multiple counters are used, as the agent is delivered to patient 101, the counters may be compared against one another to prevent or reduce the risk that the maximum time for all pump cycles threshold is corrupted or invalid. As in the example described above wherein the maximum unit dose and the redundant number of pump cycles thresholds are stored in a locked portion of a memory, the maximum time for all pump cycles threshold may likewise be stored in a locked portion of a memory, such that a hardware malfunction in the general portion the memory may not affect operation of the locked portion of the memory.

Additionally, in some examples, if the maximum time to complete all cycles threshold is reached before all cycles in the one set of pump cycles have been executed, device 100, programmer 108, and/or the external device may be configured to determine a number of pump cycles of the one set of pump cycles that were not executed in the corresponding unit period of time before the maximum time to complete all cycles threshold was reached. As described above with reference to accumulating fractional portions of sets of pump cycles, these undelivered pump cycles may also be stored and carried over to a next set of pump cycles according to which device 100 is programmed to deliver the therapeutic agent to patient 101 in the same or substantially similar manner as described above. In other examples, the undelivered pump cycles may also be accumulated and compared to a threshold, based on which an alarm may be generated to alert the clinician and/or patient 101 of an error condition. For example, the undelivered pump cycles may be accumulated and compared to a threshold that indicates device 100 is too far behind in delivering a dose of therapeutic agent to patient 101, e.g. as a percentage of the total dose or as an amount of time not delivering any of the agent, such that there may be a risk of underdosing the patient. In one example, in the event, e.g. processor 201 determines that hardware controller 214 and/or pump 208 are not function properly such that pump 208 has not delivered any of the therapeutic agent to the patient for a threshold period of time, absolute, e.g. specified by a user, or percentage of total time period, then processor 201 may trigger an alarm. In one example, if after triggering such an alarm, pump 208 under the control of hardware controller 214 recovers and begins delivering the agent to patient 101, processor 101 may turn off the alarm, but log the error, in memory 202, as well as time stamp when pump 208 recovered.

In addition to determining the above thresholds to be employed to control delivery of the therapeutic agent to patient 101, in accordance with this disclosure, a time between successive cycles of pump 208 of device 100 may be determined for delivering the one set of pump cycles based on one or more considerations. For example, the time between successive pump cycles may be determined based on one or more of a cycle time of pump 208 of device 100 (e.g., the time required for pump 208 to perform one cycle), a maximum infusion rate of the therapeutic agent to patient 101 (e.g., defined as a maximum dose of the agent to be delivered to patient 101 over a period of time), a voltage level of power source 211 of device 100 (e.g., to allow a capacitor used to source current to pump 208 to fully charge), and the maximum time for all pump cycles threshold (e.g., to assure that all cycles are delivered within the maximum allowed time). Additionally, the time between successive pump cycles may be determined based other considerations, such as how smoothly the therapeutic agent is to be delivered to patient 101 over the unit period of time associated with the one set of pump cycles.

As described above, the time between successive pump cycles may be dictated by various parameters related to components of device 100, as well as parameters associated with the therapeutic agent and/or patient 101. Accordingly, using an improper time between successive pump cycles may also have overdose or underdose implications to patient 101. For example, delivering successive pump cycles more frequently than required for pump 208 to complete each cycle may result in an underdose of the agent to patient 101. As such, the fluid delivery system in accordance with the techniques of this disclosure may further prevent or reduce the risk of improperly dosing patient 101 with the therapeutic agent by determining an appropriate time between successive pump cycles based on one or more of the above considerations.

As described above, in the event that an error condition is detected according to any of the above methods, examples according to this disclosure may include delivering the therapeutic agent to patient 101 according to one or more thresholds described above, e.g., maximum unit dose, redundant number of pump cycles, therapeutically-safe number of pump cycles, and maximum time for all pump cycles, in order to prevent overdose or underdose of the therapeutic agent to patient 101 until the clinician and/or patient 101 is able to address the error condition (e.g., by reprogramming or replacing device 100). As also described above, delivery of the therapeutic agent to patient 101 according to the one or more thresholds may be performed by processor 301, processor 201, hardware controller 214, and/or pump 208. In one example in which the error condition is such that processor 201 is able to continue to control delivery of the agent to patient 101 via hardware controller 214 and pump 208, processor 201 may retrieve the one or more thresholds, e.g., stored as data corresponding to delivery limits, from memory device 202 and direct hardware controller 214 to control pump 208 to deliver the agent to patient 101 according to the one or more thresholds. In another example in which the error condition is such that hardware of processor 201 and/or software of device 100 malfunctions, resulting in processor 201 being unable to direct hardware controller 214 to control pump 208 to deliver the therapeutic agent to patient 101 according to the one or more thresholds, hardware controller 214 may detect the error condition, access the one or more thresholds from memory device 202, and control pump 208 according to the one or more thresholds, independently of processor 201. In another example, processor 301 may indicate to hardware controller 214 the error condition, and to control hardware controller 214 to access the one or more thresholds from memory device 202 and to control pump 208 according to the one or more thresholds, independently of processor 201.

In another example, hardware controller 214 may be configured to, in the event an error condition is detected, access the one or more thresholds from memory device 202 and control pump 208 to deliver the therapeutic agent to patient 101 according to the one or more thresholds regardless of the nature of the error condition. For example, processor 201 and/or processor 301 may be configured to, upon detecting the error condition, communicate the detection of the error condition to hardware controller 214, which in turn may control pump 208 to deliver the therapeutic agent to patient 101 according to the one or more thresholds. According to this example, a method of communicating the error condition from processor 201 and/or processor 301 to hardware controller 214 may include using a specific protocol, such as a direct signaling scheme between processor 201 and/or processor 301 and hardware controller 214, writing to a memory or one or more registers (not shown) of hardware controller 214, and/or a log type-supplementary communication by which processor 201 and/or processor 301 provides hardware controller 214 with information regarding the type of error condition detected, so that hardware controller 214 may use one or more thresholds that are proper in response to the detected error condition.

According to another example, hardware controller 214 may detect an error condition when processor 201 and/or processor 301 ceases exchanging a periodic signal with hardware controller 214 (e.g., when a watchdog time-out occurs between processor 201 and/or processor 301 and hardware controller 214).

Although target site 105 for delivering the therapeutic agent as described with reference to the foregoing examples is proximate to spinal cord 106 of patient 101, other applications of the fluid delivery system in accordance with one or more aspects of this disclosure may include alternative target sites. In some examples, the alternative target sites may be proximate to different types of tissue, including, e.g., nerves, e.g., sacral, pudendal, or perineal nerves, organs, muscles, or muscle groups. In one example, catheter 103 may be positioned to deliver a therapeutic agent to a deep brain target site, or within a heart or blood vessels. Delivery of the therapeutic agent within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. In another example, catheter 103 may be positioned to deliver a therapeutic agent to a liver or lower torso vascular area. In another example, catheter 103 may be positioned to deliver insulin to a patient with diabetes. In other examples, the fluid delivery system in accordance with one or more aspects of this disclosure may deliver a therapeutic agent to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure, including those attributed to processor 201 of device 100 and processor 301 of programmer 108, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as ROM, RAM, EEPROM, NVRAM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
receiving a total dose of a therapeutic agent to be delivered to a patient by an infusion device over a total period of time;
automatically determining a plurality of individual unit dose segments from the total dose, each of the individual unit dose segments being equal to a respective fraction of the total dose, and each of the individual unit dose segments configured to be delivered to the patient by the infusion device over a respective unit period of time equal to a respective fraction of the total period of time;
automatically programming the infusion device to deliver to the patient one individual unit dose segment of the plurality of individual unit dose segments over its respective unit period of time;
delivering to the patient, by the infusion device, the one individual unit dose segment; and
determining whether an error has occurred in delivering the one individual unit dose segment to the patient.

2. The method of claim 1, further comprising:
upon determining that no error has occurred in delivering the one individual unit dose segment to the patient, automatically programming the infusion device to deliver to the patient another one of the plurality of individual unit dose segments over its respective unit period of time, delivering, by the infusion device, the other individual unit dose segment to the patient, and determining whether an error has occurred in delivering the other individual unit dose segment to the patient.

3. The method of claim 1, further comprising:
iteratively automatically programming the infusion device to deliver to the patient successive ones of the plurality of individual unit dose segments over their respective unit periods of time upon determining that no error has occurred in delivering a previous one of the plurality of individual unit dose segments to the patient, and delivering the successive individual unit dose segments until at least one of the total dose is delivered, or the total period of time elapses.

4. The method of claim 1, wherein automatically determining the plurality of individual unit dose segments is performed by a processor of an external programmer, the method further comprising transmitting the plurality of individual unit dose segments from the external programmer to the infusion device.

5. The method of claim 4, wherein automatically determining the plurality of individual unit dose segments is performed by a user using the external programmer.

6. The method of claim 4, wherein automatically determining the plurality of individual unit dose segments comprises determining, by the processor, a plurality of total dose divisions and a user selecting one of the plurality of total dose divisions determined by the processor.

7. The method of claim 1, wherein automatically determining the plurality of individual unit dose segments is performed by a processor of the infusion device.

8. The method of claim 1, wherein the infusion device comprises a processor configured to automatically program the infusion device to deliver to the patient the one individual unit dose segment over its respective unit period of time, delivering to the patient, by the infusion device, the one individual unit dose segment, and determining whether the error has occurred in delivering the one individual unit dose segment to the patient.

9. The method of claim 1, further comprising:
determining a maximum unit dose deliverable to the patient; and
comparing the one individual unit dose segment to be delivered to the patient by the infusion device to the maximum unit dose.

10. The method of claim 9, further comprising delivering to the patient, by the infusion device, at least one of the maximum unit dose or a therapeutically-safe unit dose instead of the one individual unit dose segment.

11. The method of claim 9, further comprising:
determining that the one individual unit dose segment exceeds the maximum unit dose; and
responsive to the determination, stopping delivering the therapeutic agent to the patient and generating an alarm.

12. The method of claim 9, wherein the maximum unit dose is one of a plurality of maximum unit doses, and wherein determining the maximum unit dose comprises:
determining a total maximum dose of the therapeutic agent to be delivered to the patient by the infusion device over the total period of time; and
automatically dividing the total maximum dose into the plurality of maximum unit doses, each of which is equal to a fraction of the total maximum dose corresponding to the unit period of time equal to the fraction of the total period of time, wherein the maximum unit dose comprises one of the plurality of maximum unit doses corresponding to its respective unit period of time.

13. The method of claim 12, wherein determining the total maximum dose comprises automatically determining the total maximum dose based on an infusion schedule that defines delivery of the therapeutic agent to the patient by the infusion device.

14. The method of claim 9, further comprising indicating that an error condition is present in the event that the one determined individual unit dose segment is greater than the maximum unit dose.

15. The method of claim 14, further comprising generating an alarm if it is indicated that the error condition is present.

16. The method of claim 9, further comprising storing the one individual unit dose segment in a first portion of a memory and storing the maximum unit dose in a second portion of the memory.

17. The method of claim 16, wherein the first portion of the memory is a first type of memory and the second portion of the memory is a second type of memory.

18. The method of claim 16, wherein the first portion of the memory and the second portion of the memory are contained within a single memory.

19. The method of claim 16, wherein the second portion of the memory comprises a locked memory, and wherein storing the maximum unit dose in the second portion of the memory comprises:
writing predetermined data to a first location in the locked memory to unlock a second, non-contiguous, different location in the locked memory for a predetermined period of time; and
subsequently storing, within the predetermined period of time, the maximum unit dose in the second location.

20. The method of claim 1,
wherein the total dose of the therapeutic agent to be delivered to the patient by the infusion device over the total period of time defines a total number of cycles of a pump of the infusion device to be performed over the total period of time,
wherein automatically determining the plurality of individual unit dose segments comprises automatically dividing the total number of cycles into a plurality of sets of pump cycles, each set of pump cycles being equal to a fraction of the total number of cycles configured to be delivered to the patient by the infusion device over the respective unit period of time equal to the respective fraction of the total period of time,
wherein automatically programming the infusion device to deliver the one individual unit dose segments comprises automatically programming the infusion device to deliver to the patient one of the plurality of sets of pump cycles over its respective unit period of time, and
wherein delivering the one individual unit dose segment comprises controlling the pump of the infusion device to execute the one set of pump cycles.

21. The method of claim 20, wherein determining whether the error has occurred in delivering the one individual unit dose segment comprises:
determining a maximum number of pump cycles;
decrementing a first counter corresponding to the maximum number of pump cycles and a second counter corresponding to a number of pump cycles in the one set of pump cycles, while delivering the one set of pump cycles; and
comparing a value in the first counter to a value in the second counter.

22. The method of claim 21, further comprising controlling the pump of the infusion device to execute at least one of the maximum number of pump cycles or a therapeutically-safe number of pump cycles instead of the one set of pump cycles.

23. The method of claim 21, further comprising controlling the pump to stop delivering the therapeutic agent to the patient and generating an alarm.

24. The method of claim 21, wherein the maximum number of pump cycles comprises the number of pump cycles in the one set of pump cycles.

25. The method of claim 20, wherein determining whether the error in delivering the one individual unit dose segment comprises:
determining a maximum time over which to deliver the one set of pump cycles;
decrementing a first counter corresponding to the maximum time over which to deliver the one set of pump cycles and a second counter corresponding to a number of pump cycles in the one set of pump cycles, while delivering the one set of pump cycles; and
stopping delivery of the one set of pump cycles when at least one of the first counter or the second counter reaches zero.

26. The method of claim 20 further comprising:
determining a threshold time between successive pump cycles of the one set of pump cycles for delivering the one set of pump cycles, based on one or more of the following:
a cycle time of the pump of the infusion device;
a maximum infusion rate of the therapeutic agent to the patient;
a voltage level of a power source of the infusion device; and
a time to complete all pump cycles in the one set of pump cycles.

27. The method of claim 20,
wherein automatically programming the infusion device to deliver the one set of pump cycles further comprises automatically programming the infusion device to deliver to the patient one or more undelivered pump cycles from a previously-delivered set of pump cycles, and
wherein delivering the one set of pump cycles further comprises delivering the one or more undelivered pump cycles.

28. A fluid delivery system comprising:
a pump configured to deliver a therapeutic agent to a patient;
a memory containing a total dose of the therapeutic agent to be delivered to the patient by the pump over a total period of time; and
a processor configured to automatically determining a plurality of individual unit dose segments from the total dose, each of the individual unit dose segments being equal to a respective fraction of the total dose, and each of the individual unit dose segments configured to be delivered to the patient by the pump over a respective unit period of time equal to a respective fraction of the total period of time, automatically program an infusion device comprising the pump to deliver to the patient one individual unit dose segment of the plurality of individual unit dose segments over its respective unit period of time, control the pump to deliver to the patient the one individual unit dose segment, and determine whether an error has occurred in delivering the one individual unit dose segment to the patient.

29. The system of claim 28, wherein the processor is further configured to, upon determining that no error has occurred in delivering the one individual unit dose segment to the patient, automatically program the infusion device to deliver to the patient another one of the plurality of individual unit dose segments over its respective unit period of time, control the pump to deliver the other individual unit dose segment to the patient, and determine whether an error has occurred in delivering the other individual unit dose segment to the patient.

30. The system of claim 28, wherein the processor is further configured to iteratively automatically program the infusion device to deliver to the patient successive individual unit dose segments of the plurality of individual unit dose segments over their respective unit periods of time upon determining that no error has occurred in delivering a previous one of the plurality of individual unit dose segments to the patient, and control the pump to deliver the successive individual unit dose segments until at least one of the total dose is delivered, or the total period of time elapses.

31. The system of claim 28, wherein the processor comprises a first processor and a second processor, and wherein the first processor is configured to automatically determine the plurality of individual unit dose segments, and the second processor is configured to automatically program the infusion device to deliver the one individual unit dose segment, control the pump to deliver the one individual unit dose segment, and determine whether the error has occurred in delivering the one individual unit dose segment to the patient.

32. The system of claim 31, wherein the second processor is associated with the infusion device and the first processor is associated with an external programmer configured to communicate with the infusion device.

33. The system of claim 28, wherein the processor is further configured to determine a maximum unit dose deliverable to the patient, and compare the one individual unit dose segment to be delivered to the patient by the infusion device to the maximum unit dose.

34. The system of claim 33, wherein the processor is further configured to control the pump to deliver to the patient at least one of the maximum unit dose or a therapeutically-safe unit dose instead of the one individual unit dose segment.

35. The system of claim 33, wherein the processor is further configured to:
 determine that the one individual unit dose segment exceeds the maximum unit dose; and
 responsive to the determination, control the pump to stop delivering the therapeutic agent to the patient and generate an alarm.

36. The system of claim 33, wherein the maximum unit dose is one of a plurality of maximum unit doses, and wherein the processor configured to determine the maximum unit dose comprises:
 the processor configured to determine a total maximum dose of the therapeutic agent to be delivered to the patient by the infusion device over the total period of time; and
 automatically divide the total maximum dose into the plurality of maximum unit doses, each of which is equal to a fraction of the total maximum dose corresponding to the unit period of time equal to the fraction of the total period of time, wherein the maximum unit dose comprises one of the plurality of maximum unit doses corresponding to its respective unit period of time.

37. The system of claim 36, wherein the processor configured to determine the total maximum dose comprises the processor configured to determine the total maximum dose based on an infusion schedule that defines delivery of the therapeutic agent to the patient by the infusion device.

38. The system of claim 33, wherein the processor is further configured to indicate that an error condition is present in the event that the one determined individual unit dose segment is greater than the maximum unit dose.

39. The system of claim 38, wherein the processor is further configured to generate an alarm if it is indicated that the error condition is present.

40. The system of claim 33, wherein the memory comprises a plurality of portions, and wherein the processor is further configured to store the one individual unit dose segment in a first portion of the memory, and store the maximum unit dose in a second portion of the memory.

41. The system of claim 40, wherein the first portion of the memory is a first type of memory and the second portion of the memory is a second type of memory.

42. The system of claim 40, wherein the first portion of the memory and the second portion of the memory are contained within a single memory.

43. The system of claim 40, wherein the second portion of the memory comprises a locked memory, and wherein the processor configured to store the maximum unit dose in the second portion of the memory comprises:
 the processor configured to store predetermined data in a first location in the locked memory to unlock a second, non-contiguous, different location in the locked memory for a predetermined period of time; and
 subsequently store, within the predetermined period of time, the maximum unit dose in the second location.

44. The system of claim 28,
 wherein the total dose of the therapeutic agent to be delivered to the patient by the pump over the total period of time defines a total number of cycles of the pump to be performed over the total period of time,
 wherein the processor configured to automatically determine the plurality of individual unit dose segments comprises the processor configured to automatically divide the total number of cycles into a plurality of sets of pump cycles, each set of pump cycles being equal to a fraction of the total number of cycles configured to be delivered to the patient by the infusion device over the respective unit period of time equal to the respective fraction of the total period of time,
 wherein the processor configured to automatically program the infusion device to deliver the one individual unit dose segment comprises the processor configured to automatically program the infusion device to deliver to the patient one of the plurality of sets of pump cycles over its respective unit period of time, and
 wherein the processor configured to control the pump to deliver the one individual unit dose segment comprises the processor configured to control the pump to execute the one set of pump cycles.

45. The system of claim 44, wherein the processor configured to determine whether the error has occurred in delivering the one individual unit dose segment to the patient comprises the processor configured to:
 determine a maximum number of pump cycles;
 decrement a first counter corresponding to the maximum number of pump cycles and a second counter corresponding to a number of pump cycles in the one set of pump cycles, while controlling the pump to deliver the one set of pump cycles; and
 compare a value in the first counter to a value in the second counter.

46. The system of claim 45, wherein the processor is further configured to control the pump to deliver at least one of the maximum number of pump cycles or a therapeutically-safe number of pump cycles instead of the one set of pump cycles.

47. The system of claim 45, wherein the processor is further configured to control the pump to stop delivering the therapeutic agent to the patient and generate an alarm.

48. The system of claim 45, wherein the maximum number of pump cycles comprises the number of pump cycles in the one set of pump cycles.

49. The system of claim 44, wherein the processor configured to determine whether the error has occurred in delivering the one individual unit dose segment to the patient comprises the processor configured to:
 determine a maximum time over which to deliver the one set of pump cycles;
 decrement a first counter corresponding to the maximum time over which to deliver the one set of pump cycles and a second counter corresponding to a number of pump cycles in the one set of pump cycles, while delivering the one set of pump cycles; and
 control the pump to stop executing the one set of pump cycles when at least one of the first counter or the second counter reaches zero.

50. The system of claim 44, wherein the processor is further configured to determine a threshold time between successive pump cycles of the one set of pump cycles for delivering the one set of pump cycles, based on one or more of the following:

a cycle time of the pump of the infusion device;

a maximum infusion rate of the therapeutic agent to the patient;

a voltage level of a power source of the infusion device; and a time to complete all pump cycles in the one set of pump cycles.

51. The system of claim 44, wherein the processor configured to automatically program the infusion device to deliver the one set of pump cycles comprises the processor further configured to automatically program the infusion device to deliver to the patient one or more undelivered pump cycles from a previously-delivered set of pump cycles, and wherein the processor configured to control the pump to deliver the one set of pump cycles comprises the processor further configured to control the pump to deliver the one or more undelivered pump cycles.

52. The system of claim 51, wherein the processor is configured to compare the one or more undelivered pump cycles to a threshold, and, if the one or more undelivered pump cycles exceeds the threshold, generate an alarm.

53. A computer-readable storage medium comprising instructions for causing a programmable processor to:

receive a total dose of a therapeutic agent to be delivered to a patient by an infusion device over a total period of time;

automatically determine a plurality of individual unit dose segments from the total dose, each individual unit dose segment being equal to a respective fraction of the total dose, and each individual unit dose segment configured to be delivered to the patient by the infusion device over a respective unit period of time equal to a respective fraction of the total period of time;

automatically program the infusion device to deliver to the patient one individual unit dose segment of the plurality of individual unit dose segments over its respective unit period of time;

deliver to the patient, by the infusion device, the one individual unit dose segment; and determine whether an error has occurred in delivery of the one individual unit dose segment to the patient.

54. A fluid delivery system comprising:

means for receiving a total dose of a therapeutic agent to be delivered to a patient by an infusion device over a total period of time;

means for automatically determining a plurality of individual unit dose segments from the total dose, each individual unit dose segment being equal to a respective fraction of the total dose, and each individual unit dose segment configured to be delivered to the patient, by the infusion device, over a respective unit period of time equal to a respective fraction of the total period of time;

means for automatically programming the infusion device to deliver to the patient one individual unit dose segment of the plurality of individual unit dose segments over its respective unit period of time;

means for delivering to the patient, by the infusion device, the one individual unit dose segment; and means for determining whether an error has occurred in delivering the one individual unit dose segment to the patient.

* * * * *